US009856211B2

(12) United States Patent
Bastin et al.

(10) Patent No.: US 9,856,211 B2
(45) Date of Patent: Jan. 2, 2018

(54) PHARMACEUTICAL FORMULATIONS OF HDAC INHIBITORS

(71) Applicant: TopoTarget UK LIMITED, Abingdon, Oxfordshire (GB)

(72) Inventors: Richard J. Bastin, Waterford (IE); Nicholas J. Hughes, Swindon (GB)

(73) Assignee: Topotarget UK Limited (GB)

( * ) Notice: Subject to any disclaimer, the term of this patent is extended or adjusted under 35 U.S.C. 154(b) by 0 days.

(21) Appl. No.: 14/451,928

(22) Filed: Aug. 5, 2014

(65) Prior Publication Data

US 2015/0031770 A1 Jan. 29, 2015

Related U.S. Application Data

(62) Division of application No. 11/913,191, filed as application No. PCT/GB2006/001737 on May 11, 2006, now Pat. No. 8,835,501.

(60) Provisional application No. 60/681,215, filed on May 13, 2005, provisional application No. 60/681,234, filed on May 13, 2005.

(51) Int. Cl.
  *C07C 211/21* (2006.01)
  *C07C 311/21* (2006.01)
  *A61K 9/00* (2006.01)
  *A61K 31/18* (2006.01)
  (Continued)

(52) U.S. Cl.
  CPC .......... *C07C 311/21* (2013.01); *A61K 9/0019* (2013.01); *A61K 31/18* (2013.01); *A61K 47/18* (2013.01); *A61K 47/183* (2013.01); *A61K 47/40* (2013.01)

(58) Field of Classification Search
  None
  See application file for complete search history.

(56) References Cited

U.S. PATENT DOCUMENTS 4,532,245 A 7/1985 Kompis
4,642,316 A 2/1987 Fawzi et al.
(Continued)

FOREIGN PATENT DOCUMENTS

EP 0787742 A1 8/1997
EP 1293205 A1 3/2003
(Continued)

OTHER PUBLICATIONS

Hockly et al. Suberoylanilide hydroxamic acid, a histone deacetylase inhibitor, ameliorates motor deficits in a mouse model of Huntington's disease. PNAS, vol. 100, No. 4, 2041-2046, Feb. 18, 2003.*

(Continued)

*Primary Examiner* — Karl J Puttlitz
(74) *Attorney, Agent, or Firm* — Lerner, David, Littenberg, Krumholz & Mentlik, LLP

(57) ABSTRACT

This invention pertains to pharmaceutical compositions comprising certain carbamic acid compounds (e.g., which inhibit HDAC (histone deacetylase) activity) (e.g., PXD-101, N hydroxyl-3-(3-phenylsulfamoyl-phenyl)-acrylamide)) and one or more additional ingredients selected from cyclodextrin, arginine, and meglumine. The present invention also pertains to the use of such compositions, for example, in the inhibition of HDAC, and in the treatment of conditions mediated by HDAC, cancer, proliferative conditions, psoriasis, etc.

20 Claims, 6 Drawing Sheets

(51) Int. Cl.
     A61K 47/18   (2017.01)
     A61K 47/40   (2006.01)

(56) References Cited

U.S. PATENT DOCUMENTS

| | | | |
|---|---|---|---|
| 6,071,923 | A | 6/2000 | Nudelman et al. |
| 6,342,219 | B1 | 1/2002 | Thorpe et al. |
| 6,541,661 | B1 | 4/2003 | Delorme et al. |
| 6,656,905 | B1 | 12/2003 | Mori et al. |
| 6,815,440 | B2 | 11/2004 | Thorwart et al. |
| 6,888,027 | B2 | 5/2005 | Watkins et al. |
| 7,183,298 | B2 | 2/2007 | Watkins et al. |
| RE39,850 | E | 9/2007 | Delorme et al. |
| 7,375,137 | B2 | 5/2008 | Bacopoulos et al. |
| 7,407,988 | B2 | 8/2008 | Kalvinsh et al. |
| 7,465,731 | B2 | 12/2008 | Ishibashi et al. |
| 7,491,748 | B2 | 2/2009 | Tani et al. |
| 7,495,022 | B2 | 2/2009 | Kim et al. |
| 7,557,140 | B2 | 7/2009 | Kalvinsh et al. |
| 2003/0170319 | A1 | 9/2003 | Netke et al. |
| 2003/0235588 | A1 | 12/2003 | Richon et al. |
| 2004/0018968 | A1 | 1/2004 | Sgouros et al. |
| 2004/0072735 | A1 | 4/2004 | Richon et al. |
| 2004/0077726 | A1 | 4/2004 | Watkins et al. |
| 2004/0092598 | A1 | 5/2004 | Watkins et al. |
| 2004/0127523 | A1* | 7/2004 | Bacopoulos ......... A61K 9/4866 514/352 |
| 2004/0132825 | A1 | 7/2004 | Bacopoulos et al. |
| 2004/0198830 | A1 | 10/2004 | Watkins et al. |
| 2004/0220242 | A1 | 11/2004 | Shapiro |
| 2004/0254220 | A1 | 12/2004 | Bressi et al. |
| 2005/0085515 | A1 | 4/2005 | Watkins et al. |
| 2005/0107445 | A1 | 5/2005 | Watkins et al. |
| 2005/0119305 | A1 | 6/2005 | Naka et al. |
| 2005/0124679 | A1 | 6/2005 | Kim et al. |
| 2005/0222013 | A1 | 10/2005 | Jung et al. |
| 2005/0245439 | A1 | 11/2005 | Chung |
| 2005/0288227 | A1 | 12/2005 | Marks et al. |
| 2006/0052599 | A1 | 3/2006 | Ishibashi et al. |
| 2006/0058298 | A1 | 3/2006 | Delorme et al. |
| 2006/0160897 | A1 | 7/2006 | Pelicci et al. |
| 2006/0229237 | A1 | 10/2006 | Chung et al. |
| 2006/0270016 | A1 | 11/2006 | Holm |
| 2007/0004806 | A1 | 1/2007 | Kalvinsh et al. |
| 2007/0037738 | A1 | 2/2007 | Hentsch et al. |
| 2007/0054260 | A1 | 3/2007 | Trepel et al. |
| 2007/0060614 | A1 | 3/2007 | Bacopoulos et al. |
| 2007/0110719 | A1 | 5/2007 | Holm |
| 2007/0148228 | A1 | 6/2007 | Cumming et al. |
| 2007/0232528 | A1 | 10/2007 | Franke |
| 2007/0292512 | A1 | 12/2007 | Leonard et al. |
| 2008/0004311 | A1 | 1/2008 | Hellberg |
| 2008/0045445 | A1 | 2/2008 | Chen et al. |
| 2008/0119424 | A1 | 5/2008 | Bernards et al. |
| 2008/0146623 | A1 | 6/2008 | Deziel et al. |
| 2008/0161401 | A1 | 7/2008 | Watkins et al. |
| 2008/0194690 | A1 | 8/2008 | Bastin et al. |
| 2008/0207724 | A1 | 8/2008 | Mink et al. |
| 2008/0213399 | A1 | 9/2008 | Lichenstein et al. |
| 2008/0214547 | A1 | 9/2008 | Srivastava et al. |
| 2008/0242648 | A1 | 10/2008 | Ordentlich et al. |
| 2008/0249137 | A1 | 10/2008 | Lin et al. |
| 2008/0249179 | A1 | 10/2008 | Bacopoulos et al. |
| 2008/0274120 | A1 | 11/2008 | Lichenstein et al. |
| 2008/0292616 | A1 | 11/2008 | Bates et al. |
| 2009/0012175 | A1 | 1/2009 | Bacopoulos et al. |
| 2009/0023149 | A1 | 1/2009 | Knudsen |
| 2009/0036435 | A1 | 2/2009 | Curry et al. |
| 2009/0048156 | A1 | 2/2009 | Brodie et al. |
| 2009/0060873 | A1 | 3/2009 | Sporn et al. |
| 2009/0098054 | A1 | 4/2009 | Kufe |
| 2009/0105168 | A1 | 4/2009 | Guber et al. |
| 2009/0142337 | A1 | 6/2009 | Squires |
| 2009/0186809 | A1 | 7/2009 | Hentsch et al. |
| 2009/0232800 | A1 | 9/2009 | Holm |
| 2009/0233902 | A1 | 9/2009 | Vennemann et al. |
| 2009/0246169 | A1 | 10/2009 | Vennemann et al. |
| 2009/0246198 | A1 | 10/2009 | Dong et al. |
| 2009/0270497 | A1 | 10/2009 | Buggy |
| 2009/0286862 | A1 | 11/2009 | Narita et al. |
| 2009/0298924 | A1 | 12/2009 | Davidson et al. |
| 2009/0311175 | A1 | 12/2009 | Brose |

FOREIGN PATENT DOCUMENTS

| | | |
|---|---|---|
| EP | 1426054 | 6/2004 |
| JP | H05-505813 A | 8/1993 |
| JP | 10-114681 | 5/1998 |
| JP | 2000212088 A | 8/2000 |
| JP | 2003321364 A | 11/2003 |
| JP | 2004511462 A | 4/2004 |
| WO | 9730706 A1 | 8/1997 |
| WO | 2002026696 | 4/2002 |
| WO | 02-030879 | 9/2002 |
| WO | 2002074298 A1 | 9/2002 |
| WO | 02-090534 | 11/2002 |
| WO | 2003066579 | 8/2003 |
| WO | 2003070188 A2 | 8/2003 |
| WO | 2003075929 | 9/2003 |
| WO | 2003076400 A1 | 9/2003 |
| WO | 2003082288 | 10/2003 |
| WO | 2003087057 | 10/2003 |
| WO | 2003092686 | 11/2003 |
| WO | 2004009536 A1 | 1/2004 |
| WO | 2004013130 A1 | 2/2004 |
| WO | 2004043962 A1 | 5/2004 |
| WO | 2004063146 A1 | 7/2004 |
| WO | 2004063169 A1 | 7/2004 |
| WO | 2004064727 A2 | 8/2004 |
| WO | 2004069803 A2 | 8/2004 |
| WO | 2004069823 A1 | 8/2004 |
| WO | 2004071400 A2 | 8/2004 |
| WO | 2004072047 A1 | 8/2004 |
| WO | 2004074451 A2 | 9/2004 |
| WO | 2004082638 A2 | 9/2004 |
| WO | 2004087693 A1 | 10/2004 |
| WO | 2004092115 A2 | 10/2004 |
| WO | 2004103358 A2 | 12/2004 |
| WO | 2005000901 A2 | 1/2005 |
| WO | 2005023179 A2 | 3/2005 |
| WO | 2005040106 A1 | 5/2005 |
| WO | 2005-063806 | 7/2005 |
| WO | 2006012688 A1 | 2/2006 |
| WO | 2006064121 A2 | 6/2006 |
| WO | 2006082428 A2 | 8/2006 |
| WO | 2006120456 A1 | 11/2006 |
| WO | 2007-049262 | 5/2007 |
| WO | 2007-110623 | 10/2007 |
| WO | 2008-090534 | 7/2008 |

OTHER PUBLICATIONS

Pharmacodynamic response and inhibition of growth of human tumor xenografts by the novel histone deacetylase inhibitor PXD101. Molecular Cancer Therapeutics, vol. 2, 721-728, Aug. 2003.*

Advani, R. et al., 2007, "Belinostat (PXD101) in patients with recurrent or refractory peripheral or cutaneous T-cell lymphoma: results of a phase II study," American Society for Hematology, vol. 110, Abstract No. 3453.

American Cancer Society, Inc., "Cancer Facts and Figures 2003," 2003; pp. 1-52.

Andrews et al., 2000, "Anti-malarial effect of histone deacetylation inhibitors and mammalian tumour cytodifferentiating agents," Int. J. Parasitol., vol. 30, No. 6, pp. 761-768.

Avis, K.E. et al. (editors), 1992, "Pharmaceutical Dosage Forms: parenteral medications," second edition, pp. 514-518.

Bernstein et al., 2000, "Genomewide studies of histone deacetylase function in yeast," Proc. Natl. Acad. Sci. USA, vol. 97, No. 25, pp. 13708-13713.

(56) References Cited

OTHER PUBLICATIONS

Bernhard, D. et al., 1999, "Apoptosis induced by the histone deacetylase inhibitor sodium butyrate in human leukemic lymphoblasts," FASEB J., vol. 13, No. 14, pp. 1991-2001.
Bouchain, G. et al., "Development of potential antitumor agents, synthesis and biological evaluation of a new set of sulphonamide derivatives as histone deacetylase inhibitors" J. Med. Chern., Jan. 2003; 46(5):820-830.
Chang et al., 2000, "Activation of the BRLF1 promoter and lytic cycle of Epstein-Barr virus by histone acetylation," Nucleic Acids Res., vol. 28, No. 20, pp. 3918-3925.
Dangond et al., 1998, Differential Display Cloning of a Novel Human Histone Deacetylase (HDAC3) eDNA from PHA-Activated Immune Cells, Biochem. Biophys. Res. Commun., vol. 242, No. 3, pp. 648-652.
Dorward F. Zaragoza. Side Reviews in Organic Synthesis: A guide to successful synthesis design. Weinheim: WILEY-VCH, Verlag, GMBH & Co. KGaA, 2005, Preface.
Finnin et al., 1999, "Structures of a histone deacetylase homologue bound to the TSA and SAHA inhibitors," Nature, vol. 401, pp. 188-193.
Gimseng et al., 2005, "Activity of the histone deacetylase (HDAC) inhibitor PXD101 in preclinical studies and in a phase I study in patients with advanced hematological tumors," American Society of Hematology, vol. 106, Abstract No. 3337.
Gimseng, P. et al., 2009, "Belinostat: a new broad acting antineoplastic histone deacetylase inhibitor," Expert Opin. Investig, Drugs, vol. 18, pp. 501-508.
Gimseng, P_et al., A phase I clinical trial of the histone deacetylase inhibitor belinostat in patients with advanced hematological neoplasia. Eur J Haematol. Sep. 2008, vol. 81, No. 3, pp. 170-176.
Grozinger et al., 1999, "Three proteins define a class of human histone deacetylases related to yeast Hdalp," Proc. Natl. Acad. Sci. USA, vol. 96, pp. 4868-4873.
"Guidance for Industry: S1C{R2) Dose selection for carcinogenicity studies," U.S. Department of Health and Human Services, Food and Drug Administration, Center for Drug Evaluation and Research (COER), Center for Biologics Evaluation and Research (CBER), Sep. 2008.
Hockly, E., et al, 2003, "Suberoylanilide hydroxamic acid, a histone deacetylase inhibitor, ameliorates motor deficits in a mouse model ofHntington's disease", Proc. Nat. Acad. Sci. of USA, vol. 100, pp. 2041-2046.
Hoshikawa, Y., et al., 1994, "Trichostatin A Induces Morphological Changes and Gelsolin Expression by Inhibiting Histone Deacetylase in Human Carcinoma Cell Lines," Exp. Cell. Res., vol. 214(1), pp. 189-197.
Howe, L., et al., 1999, "Histone Acetyltransferase Complexes and Their Link to Transcription," Crit. Rev. Eukaryot. Gene Expr., vol. 9(3-4), pp. 231-243.
International Preliminary Report on Patentability (IPRP) for PCT/GB2006/001737.
International Search Report (ISR) for PCT/GB2006/001737.
Onishi et al., 1996, "Antibacterial Agents That Inhibit Lipid A Biosynthesis," Science, vol. 274, pp. 939-940.
Jordan, V.C. Nature Reviews. Drug Discovery, 2, 2003, p. 205.
Kao et al., 2000, "Isolation of a novel histone deacetylase reveals that class I and class II deacetylases promote SMRT-mediated repression," Genes & Dev., vol. 14, p. 55-66.
Kasim, NA et al., "Molecular properties of WHO essential drugs and provisional biopharmaceutical classification," Mol. Pharma_ (2003) 1(1):85-96.
Kim et al., 1999, "Oxamflatin is a novel antitumor compound that inhibits mammalian histone deacetylase," Oncogene, vol. 18(15), pp. 2461-2470.
Kim, M.S., et al., 2001 "Histone deacetylases induce angiogenesis by negative regulation oftumour suppressor genes," Nature Medicine, vol. 7, No. 4, pp. 437-443.
Kimura et al., 1994, "Dual Modes of Action of Platelet-Derived Growth Factor and Its Inhibition by Trichostatin-A for DNA Synthesis in Primary Cultured Smooth Muscle Cells of Rat Aorta," Bio. Pharm. Bull., vol. 17, No. 3, pp. 399-402.
Kitamura, K., et al., 2000, "Histone deacetylase inhibitor but not arsenic trioxide differentiates acute promyelocytic leukaemia cells with t(II;17) in combination with all-trans retinoic acid," Br. J. Haematol., vol. 108(4), pp. 696-702.
Kouzarides, T., 1999, "Histone acetylases and deacetylases in cell proliferation," Curr. Opin. Genet. Dev., vol. 9, No. 1, pp. 40-48.
Kuusisto et al., 2001, "Ubiquitin-Binding Protein p62 Expression is Induced during Apoptosis and Proteasomal Inhibition in Neuronal Cells," Biochem. Biophys. Res. Commun., vol. 280, No. 1, pp. 223-228.
Laherty, C.D., et al., 1997, "Histone Deacetylases Associated with the mSin3 Corepressor Mediate Mad Transcriptional Repression," Cell, vol. 89(3), pp. 349-356.
Iavarone et al., 1999, "E2F and Histone Deacetylase Mediate Transforming Growth Factor B Repression of cdc25A during Keratinocyte Cell Cycle Arrest," Mol. Cell Bioi., vol. 19, No. 1, pp. 916-922.
Lee, J_H_et al_"Histone deacetylase inhibitor enhances 5-fluorouracil cytotoxicity by down-regulating thymidylate synthase in human cancer cells." Mol. Cancer Ther., Dec. 2006; 5(12): 3085-3095.
Lin, R.J., et al., 1998, "Role of the histone deacetylase complex in acute promyelocytic leukaemia," Nature, vol. 391 (6669), pp. 811-814.
Mackay, H. J. et al., 2007, "A phase II trial of the histone deacetylase inhibitor belinostat (PXD101) in patients with platinum resistant epithelial ovarian tumors and micropapillary/borderline (LMP) ovarian tumors. A trial of the PMH phase II consortium," AACR-NCI-EORTC Annual Meeting 2007, American Association for Cancer Research: Molecula Targets and Cancer Therapeutics.
McCaffrey et al., 1997, "Induction ofy-Globin by Histone Deacetylase Inhibitors," Blood, vol. 90, No. 5, pp. 2075-2083.
Mielnicki, L.M., et al., 1999, "Epigenetic Regulation ofGelsolin Expression in Human Breast Cancer Cell," Exp. Cell Res., vol. 249 (1), 99 161-176.
Moore, P.S. et al., "Gene expression profiling after treatment with the histone deacetylase inhibitor trichostatin A reveals altered expression of both pro- and anti-apoptotic genes in pancreatic adenocarcinoma cells," Biochem. Biophys. Acta., 2004 Sep 17, vol. 1693, No. 3, pp. 167-176.
Mura, P., et al, 2003, "Ternary systems ofnaproxen with hydroxypropyl-beta-cyclodextrin andaminoacids", Int. J. Pharm., Amsterdam, vol. 260, pp. 293-302.
Murata, T. et al., "Solubility of monoalkyl phophate in water in the presence of arginine and triton, and solubilization of methyl yellow through the mixed micelle," Prosphorus Research Bulletin (2008) 22:41-47.
Ng, H.H. and Bird, A., 2000, "Histone deacetylases: silencers for hire," Trends Biochem. Sci., vol. 25(3), pp. 121-126.
Niki et al., 1999, "A Histone Deacetylase Inhibitor, Trichostatin A, Suppresses Myofibroblastic Differentiation of Rat Hepatic Stellate Cells in Primary Culture," Hepatology, vol. 29, No. 3, pp. 858-867.
Pazin, M.J., et al., 1997, "What's up and down with histone deacetylation and transcription?," Cell, vol. 89, No. 3, pp. 325-328.
Remington's Pharmaceutical Sciences, pp. 420-425, 1980.
Saunders, N. et al, 1999 "Histone deacetylase inhibitors as potential anti-skin cancer agents," Cancer Res., vol. 59, No. 2 pp. 399-404.
Sinha et al., 2007, "A phase 1/11 study of the safety and anticancer activity of IV-administered belinostat (PXD101) plus carboplatin (C) or paclitaxel (P), or both in patients with advanced solid tumours," 2007 Annual Meeting of the American Society of Clinical Oncology, Abstract No. 3574
Spencer, V.A. and Davie, J.R., 1999, "Role of covalent modifications ofhistones in regulating gene expression," Gene, vol. 240(1), pp. 1-12.
Stapnes, C. et al., "Functional characteristics and gene expression profiles of primary acute myeloid leukaemia cells identify patient subgroups that differ in susceptibility to histone deacetylase inhibitors," Int. J. Oneal., Dec. 2007, vol. 31, No. 6, pp. 1529-1538.

(56) References Cited

OTHER PUBLICATIONS

Steele, N.L et al., A phase 1 pharmacokinetic and pharmacodynamic study of the histone deacetylase inhibitor belinostat in patients with advanced solid tumors. Clin. Cancer Res. Feb. 1, 2008, vol. 14, No. 3, pp. 804-810.
Strickley, R., 2004, "Solubilising excipients in oral and injectable formulations", Pharm. Res., vol. 21, pp. 201-230.
Sullivan, D. et al., 2006, "A Phase II Study of PXD101 in Advanced Multiple Myeloma," 2006, Annual Meeting of the American Society for Hematology, 2006, ASH Annual Meeting Abstracts, Part 1, vol. 108, Abstract 3583.
Takahashi, I., etal, 1996, "Selective inhibition ofiL-2 gene expression by trichostatin A, a potent inhibitor of mammalian histone deacetylase," J. Antibiot. (Tokyo), vol. 49, No. 5, pp. 453-457.
Taunton, J., et al., 1996, "A mammalian histone deacetylase related to the yeast transcriptional regulator Rpd3p," Science, vol. 272, pp. 408-411.
"Topotarget Aims for Top of Class," Bioventure View (2004); 19(13):11.
"TopoTarget and CuraGen advance HDAC inhibitor PXD101 into Phase II clinical trials," Press Release dated Feb. 1, 2005 and retrieved from the Internet 2006 (URL: http://www.topotarget.com/Multimedia/19-_pressrelease_01022005.pdf).
Tsuji et al., 1976, "A New Antifungal Antibiotic, Trichostatin*," J. Antibiot. (Tokyo), vol. 29, No. 1, pp. 1-6.
Ueda, H., et al., 1994, "FR901228, a novel antitumor bicyclic depsipeptide produced by Chromobacterium violaceum No. 968," J. Antibiot. (Tokyo), vol. 47(3), pp. 315-323.
Van den Wyngaert et al., "Cloning and characterization of human histone deacetylase 8," 2000, FEBS, vol. 478, pp. 77-83.
Vigushin et al., 2001, "Trichostatin A Is a Histone Deacetylase Inhibitor with Potent Antitumor Activity against Breast Cancer in vivo'," Clin. Cancer Res., vol. 7, No. 4, pp. 971-976.
Vippagunta et al. Advanced Drug Delivery Reviews, 48, 2001, p. 18.
Wedel, S. et al., "Inhibitory Effects of the HDAC Inhibitor Valproic Acid on Prostrate Cancer Growth Are Enhanced by Simultaneous Application of mTOR Inhibitor RAD001", Life Sciences, (2011), vol. 88, pp. 418-424.
Wingo, PA et al. "Cancer Statistics." CA Cancer J. Clin., 1995; 45{1}: 8-30.
Wolff et al. Burger's Medicinal Chemistry and Drug Discovery—Fifth Edition. New York: John Wiley & Sons, 1996, vol. 1, pp. 975-976.
Wong, J., et al., 1998, "Distinct requirements for chromatin assembly in transcriptional repression by thyroid hormone receptor and histone deacetylase," EMBO J., vol. 17(2), pp. 520-534.
Written Opinion of the International Searching Authority (WOISA) for PCT/GB2006/001737.
Yamagishi, S. et al., "Expression of dihydropyrimidine dehydrogenase, thymidylate synthase, p53 and p21 in metastatic liver tumor from colorectal cancer after 5-fluorouracil-based chemotherapy," Anticancer Res., Mar.-Apr. 2005, vol. 25, No. 28, pp. 1237-1242.
Yang, W.M., et al., 1996, "Transcriptional repression ofYY1 is mediated by interaction with a mammalian homolog of the yeast global regulator RPD3," Proc. Natl. Acad. Sci. USA, vol. 93, pp. 12845-12850.
Yang, W.M., et al., 1997, "Isolation and characterization of cDNAs corresponding to an additional member of the human histone deacetylase gene family," J. Bioi. Chern., vol. 272, pp. 28001-28007.
Yoshida, M. and Horinouchi, S., 1999, "Inhibition of Histone Deacetylation and Signal-Dependent Nuclear Export," Ann. N.Y. Acad. Sci., vol. 886, pp. 23-36.
Yoshida, M., Beppu, T., 1988, "Reversible arrest of proliferation of rat 3YI fibroblasts in both G1 and G2 phases by trichostatin A," Exp. Cell. Res., vol. 177, pp. 122-131.
Yoshida, M., et al., 1990a, "Potent and Specific Inhibition of Mammalian Histone Deacetylase Both in Vivo and in Vitro by Trichostatin A*," J. Bio. Chern., vol. 265(28), pp. 17174-17179.
Yoshida, M., et al., 1990b, "Structural specificity for biological activity of trichostatin A, a specific inhibitor of mammalian cell cycle with potent differentiation-inducing activity in friend leukemia cells," J. Antibiot. (Tokyo}, vol. 43 (9), pp. 1101-1106.
Zhao, J.-Y. et al., "SAHA and Curcumin Combinations Co-Enhance Histone Acetylation in Human Cancer Cells But Operate Antagonistically in Exerting Cytotoxic Effects", Journal of Asian Natural Products Research, (May 2010), vol. 12, No. 5, pp. 335-348.
Brehm,A., et al., "Retinoblastoma protein recruits histone deacetylase to repress transcription,"Nature 1998, vol. 391, pp. 597-601.
David, G., et al., "Histone deacetylase associated with mSin3A mediates repression by the acute promyelocytic leukemia-associated PLZF protein," Oncogene 1998, vol. 16(19), pp. 2549-2556.
Davie, J.R.,"Covalent modifications of histones: expression from chromatic templates,"Curr Opin. Genet. Dev.,1998 vol. 8, pp. 173-178.
Emilani, S., et al., "Characterization of a human RPD3 ortholog HDAC3," Proc. Natl. Acad. Sci. USA, 1998, vol. 95, pp. 2795-2800.
Akers, Michael J., 'Excipient-Drug Interactions in Parenteral Formulations', Journal of Pharmaceutical Sciences, vol. 91, No. 11, published in Nov. 2002, pp. 2283-2300.
Enrico Redenti, Minireview, Cyclodextrin complexes of salts of acidic drugs. Thermodynamic properties, structural features, and pharmaceutical applications, Journal of Pharmaceutical Sciences, vol. 90, Issue 8, Aug. 2001, pp. 979-986.
Hirano, A. et al., "Application of Arginine to increase the solubility of poorly water-soluble compounds," Journal of Proteomics & Bioinformatics, Proceedings of the Joint 2nd Pacific Rim International Conference on Protein Science and 4th Asian-Oceania Human Proteome Organization, Cairns, Australia, Jun. 22-26, 2008, Abstract No. 220.
Lai, J.-P. et al., "Additive Effect of Apicidin and Doxorubicin in Sulfatase 1 Expressing Hepatocellular Carcinoma In Vitro and In vivo", Journal of Hepatology, vol. 50, Issue 6, Jun. 2009, pp. 1112-1121.
Adler, J.T. et al., "Inhibition of Growth in Medullary Thyroid Cancer Cells with Histone Deacetylase Inhibitors and Lithium Chloride", Journal of Surgical Research, (2010), vol. 159, pp. 640-644.
Aravantinos G. et al., "Phase II study of docetaxel-vinorelbine in platinum-resistant, paclitaxel-pretreated ovarian cancer." Ann. Oncol., Jul. 2003; 14(7): 1094-1099.
Arnold, N. B. et al., "The Histone Deacetylase Inhibitor Suberoylanilide Hydroxamic Acid Induces Growth Inhibition and Enhances Gemcitabine-Induced Cell Death in Pancreatic Cancer", Clin. Cancer Res., (2007), vol. 13, pp. 18-26.
Banwell, C.M. et al., "Targeting 1alpha,25-dihydroxyvitamin D3 Antiproliferative Insensitivity in Breast Cancer Cells by Co-Treatment with Histone Deacetylation Inhibitors", Journal of Steroid Biochemistry & Molecular Biology, (2004), vol. 89-90, pp. 245-249.
Baradari, V. et al., "Histone Deacetylase Inhibitor MS-275 Alone or Combined with Bortezomib or Sorafenib Exhibits Strong Antiproliferative Action in Human Cholangiocarcinoma Cells", World Journal of Gastroenterology, (Sep. 7, 2007), vol. 13, No. 33, pp. 4458-4466.
Berenbaum et al., "What is Synergy?" Pharmacological Reviews, Jun. 1989; 41(2): 93-141.
Berge, S. et al. "Pharmaceutical Salts." J. Pharm. Sci., Jan. 1977; 66(1): 1-19.
Bolden, J.E. et al., "Anticancer Activities of Histone Deacetylase Inhibitors", Nature Reviews Drug Discovery, (2006), vol. 5, No. 9, pp. 769-784.
Bookman, M.A., "Extending the Platinum-Free Interval in Recurrent Ovarian Cancer. The Role of Topotecan in Second-Line Chemotherapy", The Oncologist, (1999), vol. 4, No. 2, pp. 87-94.

(56) References Cited

OTHER PUBLICATIONS

Budillon, A. et al. "Multiple-Target Drugs: Inhibitors of Heat Shock Protein 90 and of Histone Deacetylase." Curr. Drug Targets, 2005; 6(3):337-351.

Byers, T. "What Can Randomized Controlled Trials Tell Us About Nutrition and Cancer Prevention?" CA Cancer J. Clin., Nov.-Dec. 1999; 49(6):353-361.

Chou T. C. "Theoretical basis, experimental design, and computerized simulation of synergism and antagonism in drug combination studies." Pharmacol. Rev. Sep. 2006; 58(3): 621-81.

Dalgard, C.L. et al., "Evaluation of the In vitro and In vivo Antitumor Activity of Histone Deacetylase Inhibitors for the Therapy of Retinoblastoma", Clinical Cancer Research, (2008), vol. 14, pp. 3113-3123.

De Los Santos, M. et al., "Anti-estrogenic Actions of Histone Deacetylase Inhibitors in MCF-7 Breast Cancer Cells", Endocrine-Related Cancer, (2007), vol. 14, pp. 1021-1028.

De Ruijter, A.J.M. et al., "Antagonistic Effects of Sequential Administration of BL1521, a Histone Deacetylase Inhibitor, and Gemcitabine to Neuroblastoma Cells", Cancer Letters, (2006), vol. 233, No. 2, pp. 240-246.

Entin-Meer, M. et al., "AN-113, a Novel Prodrug of 4-Phenylbutyrate with Increased Anti-neoplastic Activity in Glioma Cell Lines", (2007), vol. 253, pp. 205-214.

Finn, P.W. et al., "Novel sulphonamide derivatives as inhibitors of histone deacetylase." Helvetica Chimica Acta, Jan. 2005; 88(7):1630-1657.

Granziero, L. et al. "Adoptive immunotherapy prevents prostate cancer in a transgenic animal model." Eur. J. Immunol., Apr. 1999; 29(4):1127-1138.

Hamilton T. C. et al., "Characterization of a human ovarian carcinoma cell line (NIH:OVCAR-3) with androgen and estrogen receptors." Cancer Res. Nov. 1983; 43(11): 5379-89.

Havrilesky, L.J. et al. "Weekly low-dose carboplatin and paclitaxel in the treatment of recurrent ovarian and peritoneal cancer." Gynecological Cancer; May 2003; 88(1): 51-57.

Hurtubise, A. et al., "Effect of Histone Deacetylase Inhibitor LAQ824 on Antineoplastic Action of 5-Aza-2'-deoxycytidine (Decitabine) on Human Breast Carcinoma Cells", Cancer Chemother. Pharmacol., (2006), vol. 58, pp. 618-625.

Jang, E.-R. et al., "Different Effect of Protein Kinase B/Akt and Extrcellular Signal-Regulated Kinase Inhibition on Trichostatin A-Induced Apoptosis in Epithelial Ovarian Carcinoma Cell Lines", Mol. Cell Biochem., (2011), vol. 353, pp. 1-11.

Jensen, P.B. et al. "Differential cytotoxicity of 19 anticancer agents in wild type and etoposide resistant small cell lung cancer cell lines." Br. J. Cancer, 1993; 67(2): 311-320.

Kano, Y. et al. "Cytotoxic Effects of Histone Deacetylase Inhibitor FK228 (Depsipeptide, formerly named FR901228) in Combination with Conventional Anti-Leukemia/Lymphoma Agents Against Human Leukemia/Lymphoma Cell Lines", Invest. New Drugs, (2006), vol. 25, pp. 31-40.

Khan, S.B. et al., "Analysis of Histone Deacetylase Inhibitor, Depsipeptide (FR901228), Effect on Multiple Myeloma", British Journal of Haematology, (2004), vol. 125, pp. 156-161.

Kim, J.C. et al., "In Vitro Evaluation of Histone Deacetylase Inhibitors as Combination Agents for Colorectal Cancer", Anticancer Research, (2009), vol. 29, pp. 3027-3034.

Knies-Bamforth, U. "Fight against cancer taking centre stage in Boston." Drug Discovery Today, Elsevier Science Limited, GB, 2004; 9(23):998-999.

Kuzuya K. et al., "Optimal doses of paclitaxel and carboplatin combination chemotherapy for ovarian cancer: a phase I modified continual reassessment method study." Int. J. Clin. Oncol. Dec. 2001; 6(6): 271-8.

Li, P. et al., "Coordination of PAD4 and HDAC2 in the Regulation of p53-Target Gene Expression", (2010), vol. 29, pp. 3153-3162.

Moradei, O. et al. "Histone Deacetylase Inhibitors: Latest Developments, Trends and Prospects." Curr. Med. Chem.—Anti-Cancer Agents, 2005; 5(5):529-560.

Neijt, J.P. et al. "Paclitaxel/carboplatin for the initial treatment of advanced ovarian cancer." Seminars in Oncology, Feb. 1999; 26(2 Suppl.): 78-83.

Ozols, R.F. "Recurrent Ovarian Cancer: Evidence-based Treatment." J. Clin. Oncol., Mar. 2002; 20(5): 1161-1161.

Paris M. et al., "Histone deacetylase inhibitors: from bench to clinic." J Med Chem. Mar. 27, 2008; 51(6):1505-29. Epub Feb. 5, 2008.

Pauer, L.R. et al. "Phase I Study of Oral CI-994 in Combination with Carboplatin and Paclitaxel in the Treatment of Patients with Advanced Solid Tumors." Cancer Investigation, 2004; 22(6):886-896.

Peng, C.-Y. et al., "Growth-Inhibiting Effects of Arsenic Trioxide Plus Epigenetic Therapeutic Agents on Leukemia Cell Lines", Leukemia & Lymphoma, (Feb. 2010), vol. 51, No. 2, pp. 297-303.

Plumb, J.A. et al. "Epigenetic approaches to cancer therapy." Biochem. Soc. Transactions, 2004; 32(6):1095-1097.

Plumb, J.A. et al. "Pharmacodynamic Response and Inhibition of Growth of Human Tumor Xenografts by the Novel Histone Deacetylase inhibitor PXD101." Mol. Cancer Ther, Aug. 2003; 2(8): 721-728.

Ritchie, J. et al. "The histone deacetylase inhibitor PCX101 synergises with established chemotherapeutics to inhibit tumour cell proliferation and upregulate apoptosis in vitro." Clin. Cancer Res., Dec. 2003; 9(16 Suppl.): 6105s-6106s, Abstract#A150.

Rovida, E. et al., "The c-Jun-N-terminal-Kinase Inhibitor SP600125 Enhances the Butyrate Derivative D1-Induced Apoptosis Via Caspase 8 Activation in Kasumi 1 t(8;21) Acute Myeloid Leukaemia Cells", British Journal of Haematology, (2006), vol. 135, pp. 653-659.

Shabbeer, S. et al. "Focus on deacetylation for therapeutic benefit." IDrugs, 2005; 8(2): 144-154.

Sonnemann, J. et al., "Comparative Evaluation of the Treatment Efficacy of Suberoylanilide Hydroxamic Acid (SAHA) and Paclitaxel in Ovarian Cancer Cell Lines and Primary Ovarian Cancer Cells from Patients", BMC Cancer, (2006), vol. 6, pp. 183.

Taddei, A. et al., "The Effects of Histone Deacetylase Inhibitors on Heterochromatin: Implications for Anticancer Therapy", EMBO Reports, (2005), vol. 6, No. 6, pp. 520-524.

Thigpen J. T. et al., Second-line chemotherapy for recurrent carcinoma of the ovary. Cancer. Feb. 15, 1993; 71(4 Suppl):1559-64.

Touma, S.E. et al., "Retinoic Acid and the Histone Deacetylase Inhibitor Trichostatin A Inhibit the Proliferation of Human Renal Cell Carcinoma in a Xenograft Tumor Model", Clinical Cancer Research, (2005), vol. 11, pp. 3558-3566.

Vasey, P. et al. "Phase III Randomized Trial of Docetaxel-Carboplatin Versus Paclitaxel-Carboplatin as First-line Chemotherapy for Ovarian Carcinoma." J. Natl. Cancer Inst., Nov. 2004; 96(22): 1682-1691.

Yang et al. "Knockdown of Rab25 expression by RNAi inhibits growth of human epithelial ovarian cancer cells in vitro and in vivo." Pathology, Dec. 2006; 38(6): 561-567.

\* cited by examiner

PXD101 I.V. Clearance/Dose

PHARMACEUTICAL FORMULATIONS OF HDAC INHIBITORS

RELATED APPLICATIONS

This application is a divisional of U.S. application Ser. No. 11/913,191, filed, Oct. 31, 2007, which is a national phase application of International Application No. PCT/GB2006/001737, filed May 11, 2006, which claims the benefit of and priority to U.S. provisional application Ser. No. 60/681,215, filed May 13, 2005 and to U.S. provisional application Ser. No. 60/681,234, filed May 13, 2005, the contents of each of which are incorporated herein by reference in their entireties.

TECHNICAL FIELD

This invention generally pertains to the field of pharmaceuticals and pharmacy, and more specifically to pharmaceutical compositions comprising certain carbamic acid compounds (e.g., which inhibit histone deacetylase (HDAC) activity) and one or more additional ingredients selected from cyclodextrin, arginine, and meglumine. The present invention also pertains to the use of such compositions, for example, in the inhibition of HDAC, and in the treatment of conditions mediated by HDAC.

BACKGROUND

Histone Deacetylase (HDAC)

DNA in eukaryotic cells is tightly complexed with proteins (histones) to form chromatin. Histones are small, positively charged proteins which are rich in basic amino acids (positively charged at physiological pH), which contact the phosphate groups (negatively charged at physiological pH) of DNA. There are five main classes of histones, H1, H2A, H2B, H3, and H4. The amino acid sequences of histones H2A, H2B, H3, and H4 show remarkable conservation between species, whereas H1 varies somewhat, and in some cases is replaced by another histone, e.g., H5. Four pairs of each of H2A, H2B, H3, and H4 together form a disk-shaped octomeric protein core, around which DNA (about 140 base pairs) is wound to form a nucleosome. Individual nucleosomes are connected by short stretches of linker DNA associated with another histone molecule (e.g., H1, or in certain cases, H5) to form a structure resembling a beaded string, which is itself arranged in a helical stack, known as a solenoid.

The majority of histones are synthesised during the S phase of the cell cycle, and newly synthesised histones quickly enter the nucleus to become associated with DNA. Within minutes of its synthesis, new DNA becomes associated with histones in nucleosomal structures.

A small fraction of histones, more specifically, the amino side chains thereof, are enzymatically modified by post-translational addition of methyl, acetyl, or phosphate groups, neutralising the positive charge of the side chain, or converting it to a negative charge. For example, lysine and arginine groups may be methylated, lysine groups may be acetylated, and serine groups may be phosphorylated. For lysine, the —$(CH_2)_4$—$NH_2$ sidechain may be acetylated, for example by an acetyltransferase enzyme, to give the amide —$(CH_2)_4$—$NHC(=O)CH_3$. Methylation, acetylation, and phosphorylation of amino termini of histones which extend from the nucleosomal core affect chromatin structure and gene expression. (See, for example, Spencer, V. A. and Davie, J. R., 1999, Gene, Vol. 240(1), pp. 1-12).

Acetylation and deacetylation of histones is associated with transcriptional events leading to cell proliferation and/or differentiation. Regulation of the function of transcription factors is also mediated through acetylation. Recent reviews of histone deacetylation include: Kouzarides, T., 1999, "Histone acetylases and deacetylases in cell proliferation," Curr. Opin. Genet. Dev., Vol. 9, No. 1, pp. 40-48; Pazin, M. J., et al., 1997, "What's up and down with histone deacetylation and transcription?," Cell, Vol. 89, No. 3, pp. 325-328.

The correlation between the acetylation status of histones and the transcription of genes has been known for over 30 years (see, for example, Howe, L., et al., 1999, Crit. Rev. Eukaryot. Gene Expr., Vol. 9(3-4), pp. 231-243). Certain enzymes, specifically acetylases (e.g., histone acetyltransferase, HAT) and deacetylases (e.g., histone deacetylase, HDAC), which regulate the acetylation state of histones have been identified in many organisms and have been implicated in the regulation of numerous genes, confirming the link between acetylation and transcription. See, for example, Davie, J. R., 1998, "Covalent modifications of histones: expression from chromatin templates," Curr. Opin. Genet. Dev., Vol. 8, pp. 173-178. In general, histone acetylation correlates with transcriptional activation, whereas histone deacetylation is associated with gene repression.

A growing number of histone deacetylases (HDACs) have been identified, including HDAC1 through HDAC11 (see, for example, Ng, H. H. and Bird, A., 2000, Trends Biochem. Sci., Vol. 25(3), pp. 121-126). A number of yeast histone deacetylases and plant histone deacetylases have also been identified. The first deacetylase, HDAC1, was identified in 1996 (see, for example, Taunton, J., et al., 1996, Science, Vol. 272, pp. 408 411). Subsequently, two other nuclear mammalian deacetylases were found, HDAC2 and HDAC3. See, for example: Yang, W. M., et al., 1996, Proc. Natl. Acad. Sci. USA, Vol. 93, pp. 12845-12850; Yang, W. M., et al., 1997, J. Biol. Chem., Vol. 272, pp. 28001-28007; Emiliani, S., et al., 1998, Proc. Natl. Acad. Sci. USA, Vol. 95, p. 2795-2800; Grozinger et al., 1999, Proc. Natl. Acad. Sci. USA, Vol. 96, pp. 4868-4873; Kao et al., 2000, Genes & Dev., Vol. 14, p. 55-66; Van den Wyngaert et al., 2000, FEBS, Vol. 478, pp. 77-83.

HDACs function as part of large multi-protein complexes, which are tethered to the promoter and repress transcription. Well characterised transcriptional repressors such as Mad (Laherty, C. D., et al., 1997, Cell, Vol. 89(3), pp. 349-356), pRb (Brehm, A., et al., 1998, Nature, 1998, Vol. 391, pp. 597-601), nuclear receptors (Wong, J., et al., 1998, EMBO J., Vol. 17(2), pp. 520-534) and YY1 (Yang, W. M., et al., 1997, J. Biol. Chem., Vol. 272, pp. 28001-28007) associate with HDAC complexes to exert their repressor function.

The Role of HDAC in Cell Proliferation

The study of inhibitors of histone deacetylases indicates that these enzymes play an important role in cell proliferation and differentiation. The inhibitor Trichostatin A (TSA) (Yoshida, M., et al., 1990, J. Biol. Chem., Vol. 265(28), pp. 17174-17179) causes cell cycle arrest at both G1 and G2 phases (Yoshida, M., Beppu, T., 1988, Exp. Cell. Res., Vol. 177, pp. 122-131), reverts the transformed phenotype of different cell lines, and induces differentiation of Friend leukaemia cells and others (Yoshida, M., et al., 1990, J. Antibiot. (Tokyo), Vol. 43(9), pp. 1101-1106). TSA (and SAHA) have been reported to inhibit cell growth, induce terminal differentiation, and prevent the formation of tumours in mice (Finnin et al., 1999, Nature, Vol. 401, pp. 188-193). Cell cycle arrest by TSA correlates with an increased expression of gelsolin (Hoshikawa, Y., et al., 1994, Exp. Cell. Res., Vol. 214(1), pp. 189-197), an actin regulatory protein that is down regulated in malignant breast cancer (Mielnicki, L. M., et al., 1999, *Exp. Cell. Res.*, Vol. 249(1), pp. 161-176). Similar effects on cell cycle and differentiation have been observed with a number of deacetylase inhibitors (Kim et al., 1999, *Oncogene*, Vol. 18(15), pp. 2461-2470).

The clear involvement of HDACs in the control of cell proliferation and differentiation suggests that aberrant HDAC activity may play a role in cancer. The most direct demonstration that deacetylases contribute to cancer development comes from the analysis of different acute promyelocytic leukemias (APL). In most APL subjects, a translocation of chromosomes 15 and 17 (t(15;17)) results in the expression of a fusion protein containing the N-terminal portion of PML gene product linked to most of RARα (retinoic acid receptor). In some cases, a different translocation (t(11;17)) causes the fusion between the zinc finger protein PLZF and RARα. In the absence of ligand, the wild type RARα represses target genes by tethering HDAC repressor complexes to the promoter DNA. During normal hematopoiesis, retinoic acid (RA) binds RARα and displaces the repressor complex, allowing expression of genes implicated in myeloid differentiation. The RARα fusion proteins occurring in APL subjects are no longer responsive to physiological levels of RA and they interfere with the expression of the RA-inducible genes that promote myeloid differentiation. This results in a clonal expansion of promyelocytic cells and development of leukaemia. In vitro experiments have shown that TSA is capable of restoring RA-responsiveness to the fusion RARα proteins and of allowing myeloid differentiation. These results establish a link between HDACs and oncogenesis and suggest that HDACs are potential targets for pharmaceutical intervention in APL subjects. (See, for example, Kitamura, K., et al., 2000, *Br. J. Haematol.*, Vol. 108(4), pp. 696-702; David, G., et al., 1998, *Oncogene*, Vol. 16(19), pp. 2549-2556; Lin, R. J., et al., 1998, *Nature*, Vol. 391(6669), pp. 811-814).

Furthermore, different lines of evidence suggest that HDACs may be important therapeutic targets in other types of cancer. Cell lines derived from many different cancers (prostate, colorectal, breast, neuronal, hepatic) are induced to differentiate by HDAC inhibitors (Yoshida, M. and Horinouchi, S., 1999, *Ann. N. Y. Acad. Sci.*, Vol. 886, pp. 23-36). A number of HDAC inhibitors have been studied in animal models of cancer. They reduce tumour growth and prolong the lifespan of mice bearing different types of transplanted tumours, including melanoma, leukaemia, colon, lung and gastric carcinomas, etc. (Ueda, H., et al., 1994, *J. Antibiot. (Tokyo)*, Vol. 47(3), pp. 315-323; Kim et al., 1999, *Oncogene*, Vol. 18(15), pp. 2461-2470).

Psoriasis is a common chronic disfiguring skin disease which is characterised by well-demarcated, red, hardened scaly plaques: these may be limited or widespread. The prevalence rate of psoriasis is approximately 2%, i.e., 12.5 million sufferers in the triad countries (US/Europe/Japan). While the disease is rarely fatal, it clearly has serious detrimental effects upon the quality of life of the subject: this is further compounded by the lack of effective therapies. Present treatments are either ineffective, cosmetically unacceptable, or possess undesired side effects. There is therefore a large unmet clinical need for effective and safe HDACis for this condition.

Psoriasis is a disease of complex etiology. Whilst there is clearly a genetic component, with a number of gene loci being involved, there are also undefined environmental triggers. Whatever the ultimate cause of psoriasis, at the cellular level, it is characterised by local T-cell mediated inflammation, by keratinocyte hyperproliferation, and by localised angiogenesis. These are all processes in which histone deacetylases have been implicated (see, e.g., Saunders, N. et al, 1999, *Cancer Res.*, Vol. 59, No. 2 pp. 399-404; Bernhard, D. et al., 1999, *FASEB J.*, Vol. 13, No. 14, pp. 1991-2001; Takahashi et al., 1996, *J. Antibiot. (Tokyo)*, Vol. 49, No. 5, pp. 453-457; Kim et al., 2001, *Nature Medicine*, Vol. 7, No. 4, pp. 437-443). Therefore HDAC inhibitors may be of use in therapy for psoriasis. Candidate HDACis may be screened, for example, using proliferation assays with T-cells and/or keratinocytes.

HDAC Inhibitors

One important class of HDAC inhibitors are carbamic acid compounds comprising a sulfonamide linkage, as described, for example, in Watkins, C., et al., 2002, published international (PCT) patent application number WO 02/30879. An especially promising compound is N-hydroxy-3-(3-phenylsulfamoyl-phenyl)-acrylamide (referred to herein as PXD-101).

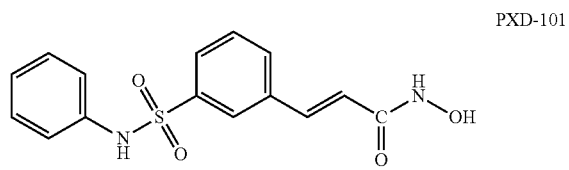 [SMILES: O=C(/C=C/c1cccc(S(=O)(=O)Nc2ccccc2)c1)NO]

PXD-101

Many potentially useful HDACis suffer from one or more formulation problems, for example, low solubility in aqueous solutions, the need to employ unsuitably high or low pH in order to effect HDACi solubilisation, physical and/or chemical instability in aqueous solutions, physical and/or chemical instability upon later dilution, etc. Compounds such as PXD-101 also suffer from these and other problems.

Thus, one aim of the present invention is the provision of improved pharmaceutical compositions (e.g., formulations and pre-formulations) which comprise PXD-101 or structurally similar compounds, which address one or more of the above and other problems.

The inventors have found particular combinations of ingredients which, surprisingly and unexpectedly, yield pharmaceutical compositions that have greatly improved properties.

These pharmaceutical compositions offer one or more of the following advantages:
(a) a greater concentration of HDACi;
(b) increased stability when in a concentrated liquid form (e.g., for storage);
(c) increased stability when in a diluted liquid form (e.g., when ready for administration);
(d) the ability to provide the composition as, for example, a ready-to-use solution, a concentrate for extemporaneous dilution, and/or a lyophilate/lyophilisate.

A number of patents and publications are cited herein in order to more fully describe and disclose the invention and the state of the art to which the invention pertains. Full citations for these references are provided herein. Each of these references is incorporated herein by reference in its entirety into the present disclosure.

SUMMARY OF THE INVENTION

One aspect of the invention pertains to pharmaceutical compositions comprising: (a) a HDACi (as defined herein), and (b) one or more of: cyclodextrin, arginine, and meglumine.

In one embodiment, the HDACi is selected from compounds of the following formula, and pharmaceutically acceptable salts, solvates, amides, esters, ethers, chemically protected forms, and prodrugs thereof:

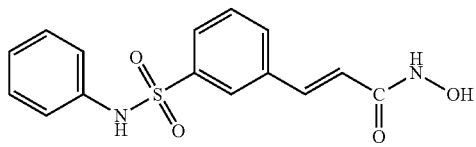

PXD-101

One aspect of the present invention pertains to a pharmaceutical composition (e.g., formulation, pre-formulation), as described herein, in a suitable container (e.g., vial, ampoule, intravenous (I.V.) infusion bag).

One aspect of the present invention pertains to a vial or ampoule containing a pharmaceutical composition (e.g., formulation, pre-formulation), as described herein.

One aspect of the present invention pertains to an intravenous (I.V.) infusion bag containing a pharmaceutical composition (e.g., formulation), as described herein.

One aspect of the present invention pertains to a solid dosage form (e.g., tablet, capsule, or gelatin tablet) containing a pharmaceutical composition containing a pharmaceutical composition (e.g., formulation), as described herein.

One aspect of the present invention pertains to a method of preparing a composition (e.g., pre-formulation, formulation) (as described herein) by combining: (a) a histone deacetylase inhibitor (HDACi) as defined herein, and (b) one or more of the following additional ingredients: cyclodextrin, arginine, and meglumine; and optionally one or more other additional pharmaceutically acceptable ingredients (as described herein).

One aspect of the present invention pertains to a method of formulating a HDACi (as described herein) comprising the step of: combining said HDACi with one or more of the following additional ingredients: cyclodextrin, arginine, and meglumine (as described herein); and optionally one or more other additional pharmaceutically acceptable ingredients (as described herein).

One aspect of the present invention pertains to a method of increasing the concentration of a HDACi (as described herein) in a pharmaceutical composition, comprising the step of: formulating said HDACi with one or more of the following additional ingredients: cyclodextrin, arginine, and meglumine (as described herein); and optionally one or more other additional pharmaceutically acceptable ingredients (as described herein).

One aspect of the present invention pertains to the pharmaceutical composition components as described herein (e.g., a HDACi; one or more of cyclodextrin, arginine, and meglumine; etc.) for use in a method of treatment of the human or animal body by therapy.

One aspect of the present invention pertains to a pharmaceutical composition (e.g., pre-formulation, formulation), as described herein, for use in a method of treatment of the human or animal body by therapy.

One aspect of the present invention pertains to use of the pharmaceutical composition components as described herein (e.g., a HDACi; one or more of cyclodextrin, arginine, and meglumine; etc.) in the manufacture of a medicament for the treatment of a condition, as described herein.

One aspect of the present invention pertains to use of a pharmaceutical composition (e.g., pre-formulation), as described herein, in the manufacture of a medicament for the treatment of a condition, as described herein.

One aspect of the present invention pertains to a method of treatment, comprising administering to a subject in need of treatment a pharmaceutical composition (e.g., formulation), as described herein.

One aspect of the present invention pertains to a method of (a) regulating (e.g., inhibiting) cell proliferation; (b) inhibiting cell cycle progression; (c) promoting apoptosis; or (d) a combination of one or more of these, in vitro or in vivo, comprising contacting a cell with a pharmaceutical composition (e.g., formulation) as described herein.

One aspect of the present invention pertains to a method of administering a HDACi, as defined herein, to a subject, comprising administering to said subject a pharmaceutical composition (e.g., formulation), as described herein.

One aspect of the present invention pertains to a kit (or kit-of-parts) comprising:
(a) a pharmaceutical composition (e.g., pre-formulation, formulation) as described herein, preferably provided in a suitable container and/or with suitable packaging; and
(b) instructions for use, for example, written instructions on how to administer the formulation, etc.

One aspect of the present invention pertains to a kit (or kit-of-parts) comprising:
(a) a pharmaceutical composition (e.g., pre-formulation) as described herein, preferably provided in a suitable container and/or with suitable packaging; and
(b) instructions for use, for example, written instructions on how to prepare a suitable pharmaceutical formulation from the composition (e.g., pre-formulation), and how to subsequently administer the formulation, etc.

As will be appreciated by one of skill in the art, features and preferred embodiments of one aspect of the invention will also pertain to other aspects of the invention.

DETAILED DESCRIPTION OF THE INVENTION

Figure 1:
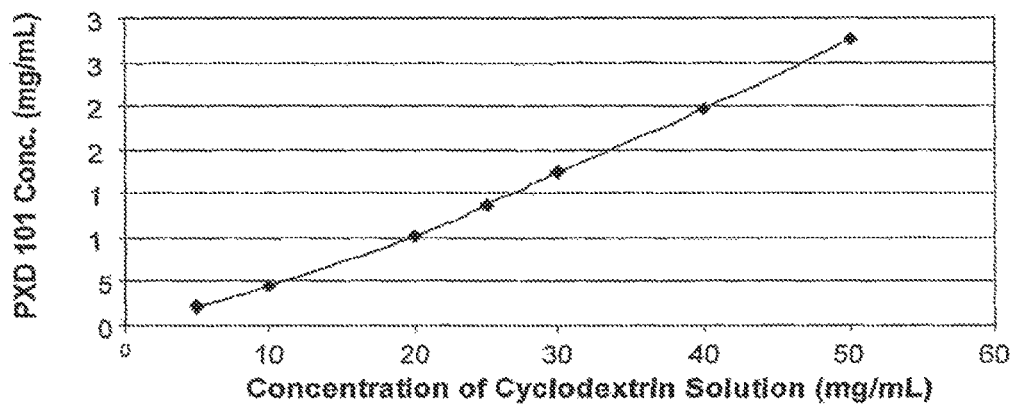
FIG. 1 is a phase solubility diagram for hydroxypropyl-β-cyclodextrin (HP-β-CD), and is a plot of HDACi (PXD-101) concentration (mg/mL) versus HP-β-CD concentration (mg/mL).

One aspect of the present invention pertains to pharmaceutical compositions which are suitable for administration to a subject (hereinafter referred to as "formulations"), as well as pharmaceutical compositions (e.g., lyophilates/lyophilisates, concentrates, etc.) from which such formulations may be prepared (hereinafter referred to as "pre-formulations").

Administration

In one embodiment, the administration is parenteral administration.

In one embodiment, the administration is administration by injection, including, for example, subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal injection.

In one embodiment, the administration is intravenous administration. In one embodiment, the administration is administration by intravenous injection. In one embodiment, the administration is administration by infusion. In one embodiment, the administration is administration by intravenous infusion.

For example, in one preferred embodiment, the composition (e.g., pre-formulation) is added to a saline or glucose solution (e.g., into a typical 1 L intravenous saline or glucose bag), and the resulting composition (e.g., formulation) is used for administration by intravenous infusion.

"Infusion" differs from "injection" in that the term "infusion" describes the passive introduction of a substance (e.g., a fluid, HDACi, electrolyte, etc.) into a vein or tissues by gravitational force, whereas the term "injection" describes the active introduction of a substance into a vein or tissues by additional forces, e.g., the pressure in a syringe.

Administration can be effected in one dose, continuously or intermittently (e.g., in divided doses at appropriate intervals) throughout the course of treatment. Methods of determining the most effective means and dosage of administration are well known to those of skill in the art and will vary with the particular formulation used for therapy, the purpose of the therapy, the target cell(s) being treated, and the subject being treated. Single or multiple administrations can be carried out with the dose level and pattern being selected by the treating physician, clinician, or veterinarian.

The Subject

In one embodiment, the subject is an animal; a mammal; a placental mammal, a rodent (e.g., a guinea pig, a hamster, a rat, a mouse), murine (e.g., a mouse), a lagomorph (e.g., a rabbit), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human. In one embodiment, the subject is a human, i.e., a living human, including a living human foetus, a living human child, and a living human adult.

Components

The pharmaceutical compositions of the present invention comprise, at least, the following components:
(a) a HDACi as defined herein; and
(b) one or more of the following additional ingredients: cyclodextrin, arginine, and meglumine.

In one embodiment, (b) is cyclodextrin. In one embodiment, (b) is arginine. In one embodiment, (b) is meglumine. In one embodiment, (b) is cyclodextrin and arginine. In one embodiment, (b) is cyclodextrin and meglumine. In one embodiment, (b) is arginine and meglumine. In one embodiment, (b) is cyclodextrin, arginine, and meglumine. Each of these components is discussed in more detail below.

In one embodiment, the pharmaceutical composition further comprises one or more other additional ingredients (e.g., pharmaceutically acceptable carriers, etc.).

The HDACi

The pharmaceutical compositions of the present invention comprise a HDACi which is a carbamic acid compound comprising a sulfonamide linkage. Examples of such HDACis are shown, for example, in Watkins et al., 2002, international (PCT) patent publication number WO 02/30879.

In one embodiment, the HDACi is a carbamic acid compound comprising a sulfonamide linkage, as defined in Watkins et al., 2002, published international (PCT) patent application number WO 02/30879.

In one embodiment, the HDACi is selected from compounds of the following formula:

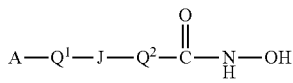

wherein:
A is independently:
  $C_{6-20}$carboaryl, or
  $C_{5-20}$heteroaryl,
  and is unsubstituted or substituted;
$Q^1$ is independently:
  a covalent bond,
  $C_{1-7}$alkylene
  $C_{2-7}$alkenylene, or
  and is unsubstituted or substituted;
J is independently:
  —NR$^N$—S(=O)$_2$—, or
  —S(=O)$_2$—NR$^N$—;
R$^N$ is independently:
  —H,
  $C_{1-7}$alkyl,
  $C_{3-20}$heterocyclyl,
  $C_{6-20}$carboaryl, $C_{5-20}$heteroaryl,
$C_{6-20}$carboaryl-$C_{1-7}$alkyl, or
$C_{5-20}$heteroaryl-$C_{1-7}$alkyl,
and is unsubstituted or substituted;
$Q^2$ is independently:
$C_{6-20}$carboarylene,
$C_{5-20}$heteroarylene,
$C_{6-20}$carboarylene-$C_{1-7}$alkylene,
$C_{5-20}$heteroarylene-$C_{1-7}$alkylene,
$C_{6-20}$carboarylene-$C_{2-7}$alkenylene,
$C_{5-20}$heteroarylene-$C_{2-7}$alkenylene,
$C_{1-7}$alkylene-$C_{6-20}$carboarylene,
$C_{1-7}$alkylene-$C_{5-20}$heteroarylene,
$C_{2-7}$alkenylene-$C_{6-20}$carboarylene,
$C_{2-7}$alkenylene-$C_{5-20}$heteroarylene,
$C_{1-7}$alkylene-$C_{6-20}$carboarylene-$C_{1-7}$alkylene,
$C_{1-7}$alkylene-$C_{5-20}$heteroarylene-$C_{1-7}$alkylene,
$C_{2-7}$alkenylene-$C_{6-20}$carboarylene-$C_{1-7}$alkylene,
$C_{2-7}$alkenylene-$C_{5-20}$heteroarylene-$C_{1-7}$alkylene,
$C_{1-7}$alkylene-$C_{6-20}$carboarylene-$C_{2-7}$alkenylene,
$C_{1-7}$alkylene-$C_{5-20}$heteroarylene-$C_{2-7}$alkenylene,
$C_{2-7}$alkenylene-$C_{6-20}$carboarylene-$C_{2-7}$alkenylene, or
$C_{2-7}$alkenylene-$C_{5-20}$heteroarylene-$C_{2-7}$alkenylene,
and is unsubstituted or substituted;
and pharmaceutically acceptable salts, solvates, amides, esters, ethers, chemically protected forms, and prodrugs thereof.

In one embodiment, the HDACi is also an HDAC inhibitor.

One of ordinary skill in the art is readily able to determine whether or not a candidate HDACi is an HDAC inhibitor. For example, assays which may conveniently be used to assess HDAC inhibition are described in Watkins et al., 2002, international (PCT) patent publication number WO 02/30879.

In a preferred embodiment, the carbamic acid group, —C(=O)NHOH, is unmodified (e.g., is not an ester).

It is not intended that $Q^1$ and $Q^2$ are directly linked to one another. It is not intended that $Q^1$ and $R^N$ are directly linked to one another. It is not intended that Q2 and $R^N$ are directly linked to one another. It is not intended that A and $R^N$ are directly linked to one another. It is not intended that A and $Q^2$ are directly linked to one another.

The HDACi: Group A

The group A is independently $C_{6-20}$carboaryl or $C_{5-20}$heteroaryl and is unsubstituted or substituted.

In one embodiment, A is independently $C_{6-10}$carboaryl or $C_{5-6}$heteroaryl, and is unsubstituted or substituted.

In one embodiment, A is independently $C_6$carboaryl or $C_{5-6}$heteroaryl, and is unsubstituted or substituted.

In one embodiment, A is independently derived from: benzene, naphthalene, carbazole, pyridine, pyrrole, furan, thiophene, or thiazole; and is unsubstituted or substituted.

The phrase "derived from," as used in this context, pertains to compounds which have the same ring atoms, and in the same orientation/configuration, as the parent cyclic group, and so include, for example, hydrogenated (e.g., partially saturated, fully saturated), carbonyl-substituted, and other substituted derivatives. For example, "pyrrolidone" and "N-methyl pyrrole" are both derived from "pyrrole".

In one embodiment, A is independently: phenyl, naphthyl, carbazolyl, pyridinyl, pyrrolyl, furanyl, thienyl, or thiazolyl; and is unsubstituted or substituted.

In one embodiment, A is independently phenyl, and is unsubstituted or substituted (e.g., with 1, 2, 3, 4, or 5 substituents).

In one embodiment, A is independently:

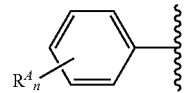

In one embodiment, n is 0, 1, 2, 3, 4, or 5. In one embodiment, n is 0, 1, 2, 3, or 4. In one embodiment, n is 0, 1, 2, or 3. In one embodiment, n is 0, 1, or 2. In one embodiment, n is 0 or 1. In one embodiment, n is 1, 2, 3, 4, or 5. In one embodiment, n is 1, 2, 3, or 4. In one embodiment, n is 1, 2, or 3. In one embodiment, n is 1, or 2. In one embodiment, n is 5. In one embodiment, n is 4. In one embodiment, n is 3. In one embodiment, n is 2. In one embodiment, n is 1. In one embodiment, n is 0.

In one embodiment, each of the substituents, $R^A$, if present, is independently as defined below under the heading "The HDACi: Substituents".

In one embodiment, A is unsubstituted.

The HDACi: Group $Q^1$

The group $Q^1$ is independently a covalent bond, $C_{1-7}$alkylene, or $C_{2-7}$alkenylene, and is unsubstituted or substituted.

In one embodiment, $Q^1$ is independently a covalent bond or $C_{1-7}$alkylene, and is unsubstituted or substituted.

The term "alkylene," as used herein, pertains to bidentate moieties obtained by removing two hydrogen atoms, either both from the same carbon atom, or one from each of two different carbon atoms, of a saturated hydrocarbon compound (a compound consisting of carbon atoms and hydrogen atoms) having from 1 to 20 carbon atoms (unless otherwise specified), which may be aliphatic (i.e., linear or branched) or alicyclic (i.e., cyclic but not aromatic).

The term "alkenylene," as used herein, pertains to bidentate moieties obtained by removing two hydrogen atoms, either both from the same carbon atom, or one from each of two different carbon atoms, of a hydrocarbon compound (a compound consisting of carbon atoms and hydrogen atoms) having from 1 to 20 carbon atoms (unless otherwise specified) and having at least one carbon-carbon double bond, and which may be aliphatic (i.e., linear or branched) or alicyclic (i.e., cyclic but not aromatic).

In one embodiment, $Q^1$ is independently $C_{1-7}$alkylene or $C_{2-7}$alkenylene, and is unsubstituted or substituted.

In one embodiment, $Q^1$ is independently $C_{1-4}$alkylene or $C_{2-4}$alkenylene, and is unsubstituted or substituted.

In one embodiment, $Q^1$ is independently $C_{1-3}$alkylene or $C_{2-3}$alkenylene, and is unsubstituted or substituted.

In one embodiment, $Q^1$ is independently $C_{2-7}$alkylene or $C_{2-7}$alkenylene, and is unsubstituted or substituted.

In one embodiment, $Q^1$ is independently $C_{2-4}$alkylene or $C_{2-4}$alkenylene, and is unsubstituted or substituted.

In one embodiment, $Q^1$ is independently $C_{2-3}$alkylene or $C_{2-3}$alkenylene, and is unsubstituted or substituted.

In one embodiment, $Q^1$ is independently $C_2$alkylene or $C_2$alkenylene, and is unsubstituted or substituted.

In one embodiment, $Q^1$ is independently $C_{1-7}$alkylene, and is unsubstituted or substituted.

In one embodiment, $Q^1$ is independently $C_{1-4}$alkylene, and is unsubstituted or substituted.

In one embodiment, $Q^1$ is independently $C_{1-3}$alkylene, and is unsubstituted or substituted.

In one embodiment, $Q^1$ is independently $C_{2-7}$alkylene, and is unsubstituted or substituted.

In one embodiment, $Q^1$ is independently $C_{2-4}$alkylene, and is unsubstituted or substituted.

In one embodiment, $Q^1$ is independently $C_{2-3}$alkylene, and is unsubstituted or substituted.

In one embodiment, $Q^1$ is independently $C_2$alkylene, and is unsubstituted or substituted.

In one embodiment, $Q^1$ is independently aliphatic. In one embodiment, $Q^1$ is independently linear. In one embodiment, $Q^1$ is independently branched.

In one embodiment, $Q^1$ is independently unsubstituted.

All plausible combinations of the embodiments described above are explicitly disclosed herein, as if each combination was individually and explicitly recited.

In one embodiment, $Q^1$ is independently: a covalent bond, —$CH_2$—, —$(CH_2)_2$—, —$(CH_2)_3$—, —$(CH_2)_4$—, —CH=CH—, —CH=CHCH$_2$—, —CH$_2$CH=CHCH$_2$—, —CH=CHCH=CH—, or —CH$_2$CH$_2$CH=CH—.

In one embodiment, $Q^1$ is independently: a covalent bond, —CH$_2$—, —CH$_2$CH$_2$—, or —CH=CH—. In one embodiment, $Q^1$ is independently: a covalent bond, —CH$_2$CH$_2$—, or —CH=CH—. In one embodiment, $Q^1$ is independently: a covalent bond. In one embodiment, $Q^1$ is independently: —CH$_2$CH$_2$— or —CH=CH—. In one embodiment, $Q^1$ is independently: —CH$_2$CH$_2$—.

The HDACi: Group J

The group J is independently —NR$^N$—S(=O)$_2$— or —S(=O)$_2$NR$^N$—.

In one embodiment, J is independently —NR$^N$—S(=O)$_2$— ("reverse sulfonamide"). In one embodiment, J is independently —S(=O)$_2$—NR$^N$— ("forward sulfonamide").

The HDACi: Group $R^N$

The group $R^N$ is independently:
—H,
$C_{1-7}$alkyl
$C_{3-20}$heterocyclyl,
$C_{6-20}$carboaryl,
$C_{5-20}$heteroaryl,
$C_{6-20}$carboaryl-$C_{1-7}$alkyl, or
$C_{5-20}$heteroaryl-$C_{1-7}$alkyl,
and is unsubstituted or substituted.

In one embodiment, $R^N$ is independently:
—H,
$C_{1-7}$alkyl
$C_{6-20}$carboaryl, or
$C_{6-20}$carboaryl-$C_{1-7}$alkyl,
and is unsubstituted or substituted.

In one embodiment, the or each $C_{6-20}$carboaryl group is a $C_{6-10}$carboaryl group. In one embodiment, the or each $C_{5-20}$heteroaryl group is a $C_{5-10}$heteroaryl group.

In one embodiment, the or each $C_{6-20}$carboaryl group is a $C_6$carboaryl group. In one embodiment, the or each $C_{5-20}$heteroaryl group is a $C_{5-6}$heteroaryl group.

In one embodiment, the $C_{3-20}$heterocyclyl group is a $C_{3-10}$heterocyclyl group. In one embodiment, the $C_{3-20}$heterocyclyl group is a $C_{5-7}$heterocyclyl group.

In one embodiment, the or each $C_{1-7}$alkyl group is a $C_{1-4}$alkyl group.

In one embodiment, the or each $C_{1-7}$alkyl group is a $C_{1-3}$alkyl group.

In one embodiment, the or each $C_{1-7}$alkyl group is a $C_{1-2}$alkyl group.

In one embodiment, the or each alkyl group is independently aliphatic.

In one embodiment, the or each alkyl group is independently linear.

In one embodiment, the or each alkyl group is independently branched.

In one embodiment, the or each alkyl group is independently saturated.

In one embodiment, the or each alkyl group is independently partially saturated.

In one embodiment, $R^N$ is independently unsubstituted.

All plausible combinations of the embodiments described above are explicitly disclosed herein, as if each combination was individually and explicitly recited.

In one embodiment, $R^N$ is independently: —H or $C_{1-7}$alkyl, and is unsubstituted or substituted.

In one embodiment, $R^N$ is independently: —H or unsubstituted $C_{1-4}$alkyl.

In one embodiment, $R^N$ is independently: —H or unsubstituted saturated $C_{1-4}$alkyl.

In one embodiment, $R^N$ is independently: —H or unsubstituted saturated aliphatic $C_{1-4}$alkyl.

In one embodiment, $R^N$ is independently: —H, -Me, -Et, -nPr, -iPr, -nBu, -sBu, -iBu, or -tBu. In one embodiment, $R^N$ is independently: —H, -Me, or -Et. In one embodiment, $R^N$ is independently: —H or -Me.

The HDACi: Group $Q^2$

The group $Q^2$ is independently:
$C_{6-20}$carboarylene,
$C_{5-20}$heteroarylene,
$C_{6-20}$carboarylene-$C_{1-7}$alkylene,
$C_{5-20}$heteroarylene-$C_{1-7}$alkylene,
$C_{6-20}$carboarylene-$C_{2-7}$alkenylene,
$C_{5-20}$heteroarylene-$C_{2-7}$alkenylene,
$C_{1-7}$alkylene-$C_{6-20}$carboarylene,
$C_{1-7}$alkylene-$C_{5-20}$heteroarylene,
$C_{2-7}$alkenylene-$C_{6-20}$carboarylene,
$C_{2-7}$alkenylene-$C_{5-20}$heteroarylene,
$C_{1-7}$alkylene-$C_{6-20}$carboarylene-$C_{1-7}$alkylene,
$C_{1-7}$alkylene-$C_{5-20}$heteroarylene-$C_{1-7}$alkylene,
$C_{2-7}$alkenylene-$C_{6-20}$carboarylene-$C_{1-7}$alkylene,
$C_{2-7}$alkenylene-$C_{5-20}$heteroarylene-$C_{1-7}$alkylene,
$C_{1-7}$alkylene-$C_{6-20}$carboarylene-$C_{2-7}$alkenylene,
$C_{1-7}$alkylene-$C_{5-20}$heteroarylene-$C_{2-7}$alkenylene,
$C_{2-7}$alkenylene-$C_{6-20}$carboarylene-$C_{2-7}$alkenylene, or
$C_{2-7}$alkenylene-$C_{5-20}$heteroarylene-$C_{2-7}$alkenylene,
and is unsubstituted or substituted.

In one embodiment, $Q^2$ is independently:
$C_{6-10}$carboarylene,
$C_{5-10}$heteroarylene,
$C_{6-10}$carboarylene-$C_{1-7}$alkylene,
$C_{5-10}$heteroarylene-$C_{1-7}$alkylene,
$C_{6-10}$carboarylene-$C_{2-7}$alkenylene,
$C_{5-10}$heteroarylene-$C_{2-7}$alkenylene,
$C_{1-7}$alkylene-$C_{6-10}$carboarylene,
$C_{1-7}$alkylene-$C_{5-10}$heteroarylene,
$C_{2-7}$alkenylene-$C_{6-10}$carboarylene,
$C_{2-7}$alkenylene-$C_{5-10}$heteroarylene,
$C_{1-7}$alkylene-$C_{6-10}$carboarylene-$C_{1-7}$alkylene,
$C_{1-7}$alkylene-$C_{5-10}$heteroarylene-$C_{1-7}$alkylene,
$C_{2-7}$alkenylene-$C_{6-10}$carboarylene-$C_{1-7}$alkylene,
$C_{2-7}$alkenylene-$C_{5-10}$heteroarylene-$C_{1-7}$alkylene,
$C_{1-7}$alkylene-$C_{6-10}$carboarylene-$C_{2-7}$alkenylene,
$C_{1-7}$alkylene-$C_{5-10}$heteroarylene-$C_{2-7}$alkenylene,
$C_{2-7}$alkenylene-$C_{6-10}$carboarylene-$C_{2-7}$alkenylene, or
$C_{2-7}$alkenylene-$C_{5-10}$heteroarylene-$C_{2-7}$alkenylene,
and is unsubstituted or substituted.

In one embodiment, $Q^2$ is independently:
$C_6$carboarylene,
$C_{5-6}$heteroarylene,
$C_6$carboarylene-$C_{1-7}$alkylene,
$C_{5-6}$heteroarylene-$C_{1-7}$alkylene,
$C_6$carboarylene-$C_{2-7}$alkenylene, $C_{5-6}$heteroarylene-$C_{2-7}$alkenylene,
$C_{1-7}$alkylene-$C_6$carboarylene,
$C_{1-7}$alkylene-$C_{5-6}$heteroarylene,
$C_{2-7}$alkenylene-$C_6$carboarylene,
$C_{2-7}$alkenylene-$C_{5-6}$heteroarylene,
$C_{1-7}$alkylene-$C_6$carboarylene-$C_{1-7}$alkylene,
$C_{1-7}$alkylene-$C_{5-6}$heteroarylene-$C_{1-7}$alkylene,
$C_{2-7}$alkenylene-$C_6$carboarylene-$C_{1-7}$alkylene,
$C_{2-7}$alkenylene-$C_{5-6}$heteroarylene-$C_{1-7}$alkylene,
$C_{1-7}$alkylene-$C_6$carboarylene-$C_{2-7}$alkenylene,
$C_{1-7}$alkylene-$C_{5-6}$heteroarylene-$C_{2-7}$alkenylene,
$C_{2-7}$alkenylene-$C_6$carboarylene-$C_{2-7}$alkenylene, or
$C_{2-7}$alkenylene-$C_{5-6}$heteroarylene-$C_{2-7}$alkenylene,
and is unsubstituted or substituted.

In one embodiment, $Q^2$ is independently:
phenylene,
phenylene-$C_{1-7}$alkylene,
phenylene-$C_{2-7}$alkenylene,
$C_{1-7}$alkylene-phenylene,
$C_{2-7}$alkenylene-phenylene,
$C_{1-7}$alkylene-phenylene-$C_{1-7}$alkylene,
$C_{2-7}$alkenylene-phenylene-$C_{1-7}$alkylene,
$C_{1-7}$alkylene-phenylene-$C_{2-7}$alkenylene, or
$C_{2-7}$alkenylene-phenylene-$C_{2-7}$alkenylene,
and is unsubstituted or substituted.

In one embodiment, $Q^2$ is independently:
phenylene,
phenylene-$C_{1-7}$alkylene, or
phenylene-$C_{2-7}$alkenylene,
and is unsubstituted or substituted.

In one embodiment, the or each $C_{1-7}$alkylene group is a $C_{1-4}$alkylene group. In one embodiment, the or each $C_{1-7}$alkylene group is a $C_{1-3}$alkylene group. In one embodiment, the or each $C_{1-7}$alkylene group is a $C_{1-2}$alkylene group. In one embodiment, the or each $C_{1-7}$alkylene group is a $C_2$alkylene group.

In one embodiment, the or each $C_{1-7}$alkenylene group is a $C_{2-4}$alkenylene group. In one embodiment, the or each $C_{1-7}$alkenylene group is a $C_{2-3}$alkenylene group. In one embodiment, the or each $C_{1-7}$alkenylene group is a $C_2$alkenylene group.

In one embodiment, the phenylene linkage is meta or para. In one embodiment, the phenylene linkage is meta. In one embodiment, the phenylene linkage is para.

In one embodiment, $Q^2$ is independently ortho-, meta-, or para-phenylene-ethylene, and is unsubstituted or substituted.

In one embodiment, $Q^2$ is independently ortho-, meta-, or para-phenylene-ethenylene, and is unsubstituted or substituted.

In one embodiment, the ethenylene is cis- or trans-ethenylene. In one embodiment, the ethenylene is trans-ethenylene. In one embodiment, $Q^2$ is independently meta-phenylene-ethenylene, and is unsubstituted or substituted.

In one embodiment, $Q^2$ is unsubstituted.

All plausible combinations of the embodiments described above are explicitly disclosed herein, as if each combination was individually and explicitly recited.

In one embodiment, $Q^2$ is independently:

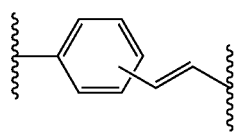

In one embodiment, $Q^2$ is independently:

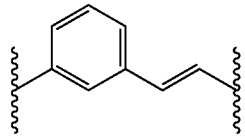 [SMILES: */C=C/c1cccc(*)c1]

The HDACi: Substituents

In one embodiment, each of the substituents (e.g., on A, $Q^1$, $R^N$, $Q^2$) (e.g., $R^A$), if present, is independently selected from:
carboxylic acid; (2) ester; (3) amido or thioamido; (4) acyl; (5) halo; (6) cyano; (7) nitro; (8) hydroxy; (9) ether; (10) thiol; (11) thioether; (12) acyloxy; (13) carbamate; (14) amino; (15) acylamino or thioacylamino; (16) aminoacylamino or aminothioacylamino; (17) sulfonamino; (18) sulfonyl; (19) sulfonate; (20) sulfonamido; (21) oxo; (22) imino; (23) hydroxyimino; (24) $C_{5-20}$aryl-$C_{1-7}$alkyl; (25) $C_{5-20}$aryl; (26) $C_{3-20}$heterocyclyl; (27) $C_{1-7}$alkyl; (28) bidentate di-oxy groups.

In one embodiment, each of the substituents (e.g., on A, $Q^1$, $R^N$, $Q^2$) (e.g., $R^A$), if present, is independently selected from:
(1) —C(=O)OH;
(2) —C(=O)OR$^1$, wherein R$^1$ is independently as defined in (24), (25), (26) or (27);
(3) —C(=O)NR$^2$R$^3$ or —C(=S)NR$^2$R$^3$, wherein each of R$^2$ and R$^3$ is independently —H; or as defined in (24), (25), (26) or (27); or R$^2$ and R$^3$ taken together with the nitrogen atom to which they are attached form a ring having from 3 to 7 ring atoms;
(4) —C(=O)R$^4$, wherein R$^4$ is independently —H, or as defined in (24), (25), (26) or (27);
(5) —F, —Cl, —Br, —I;
(6) —CN;
(7) —NO$_2$;
(8) —OH;
(9) —OR$^5$, wherein R$^5$ is independently as defined in (24), (25), (26) or (27);
(10) —SH;
(11) —SR$^6$, wherein R$^6$ is independently as defined in (24), (25), (26) or (27);
(12) —OC(=O)R$^7$, wherein R$^7$ is independently as defined in (24), (25), (26) or (27);
(13) —OC(=O)NR$^8$R$^9$, wherein each of R$^8$ and R$^9$ is independently —H; or as defined in (24), (25), (26) or (27); or R$^8$ and R$^9$ taken together with the nitrogen atom to which they are attached form a ring having from 3 to 7 ring atoms;
(14) —NR$^{10}$R$^{11}$, wherein each of R$^{10}$ and R$^{11}$ is independently —H; or as defined in (24), (25), (26) or (27); or R$^{10}$ and R$^{11}$ taken together with the nitrogen atom to which they are attached form a ring having from 3 to 7 ring atoms;
(15) —NR$^{12}$C(=O)R$^{13}$ or —NR$^{12}$C(=S)R$^{13}$, wherein R$^{12}$ is independently —H; or as defined in (24), (25), (26) or (27); and R$^{13}$ is independently —H, or as defined in (24), (25), (26) or (27);
(16) —NR$^{14}$C(=O)NR$^{15}$R$^{16}$ or —NR$^{14}$C(=S)NR$^{15}$R$^{16}$, wherein R$^{14}$ is independently —H; or as defined in (24), (25), (26) or (27); and each of R$^{15}$ and R$^{16}$ is independently —H; or as defined in (24), (25), (26) or (27); or R$^{15}$ and R$^{16}$ taken together with the nitrogen atom to which they are attached form a ring having from 3 to 7 ring atoms;

(17) —NR$^{17}$SO$_2$R$^{18}$, wherein R$^{17}$ is independently —H; or as defined in (24), (25), (26) or (27); and R$^{18}$ is independently —H, or as defined in (24), (25), (26) or (27);

(18) —SO$_2$R$^{19}$, wherein R$^{19}$ is independently as defined in (24), (25), (26) or (27);

(19) —OSO$_2$R$^{20}$ and wherein R$^{20}$ is independently as defined in (24), (25), (26) or (27);

(20) —SO$_2$NR$^{21}$R$^{22}$, wherein each of R$^{21}$ and R$^{22}$ is independently —H; or as defined in (24), (25), (26) or (27); or R$^{21}$ and R$^{22}$ taken together with the nitrogen atom to which they are attached form a ring having from 3 to 7 ring atoms;

(21) =O;

(22) =NR$^{23}$, wherein R$^{23}$ is independently —H; or as defined in (24), (25), (26) or (27);

(23) =NOR$^{24}$, wherein R$^{24}$ is independently —H; or as defined in (24), (25), (26) or (27);

(24) C$_{5-20}$aryl-C$_{1-7}$alkyl, for example, wherein C$_{5-20}$aryl is as defined in (25); unsubstituted or substituted, e.g., with one or more groups as defined in (1) to (28);

(25) C$_{5-20}$aryl, including C$_{6-20}$carboaryl and C$_{5-20}$heteroaryl; unsubstituted or substituted, e.g., with one or more groups as defined in (1) to (28);

(26) C$_{3-20}$heterocyclyl; unsubstituted or substituted, e.g., with one or more groups as defined in (1) to (28);

(27) C$_{1-7}$alkyl, C$_{2-7}$alkenyl, C$_{2-7}$alkynyl, C$_{3-7}$cycloalkyl, C$_{3-7}$cycloalkenyl, C$_{3-7}$cycloalkynyl, unsubstituted or substituted, e.g., with one or more groups as defined in (1) to (26); and

(28) —O—R$^{25}$—O—, wherein R$^{25}$ is independently saturated C$_{1-3}$alkyl, and is independently unsubstituted or substituted with one or more (e.g., 1, 2, 3, 4) substituents as defined in (5).

Some examples of (27) include the following:

halo-C$_{1-7}$alkyl;

amino-C$_{1-7}$alkyl (e.g., —(CH$_2$)$_w$-amino, w is 1, 2, 3, or 4);

amido-C$_{1-7}$alkyl (e.g., —(CH$_2$)$_w$-amido, w is 1, 2, 3, or 4);

acylamido-C$_{1-7}$alkyl (e.g., —(CH$_2$)$_w$-acylamido, w is 1, 2, 3, or 4);

carboxy-C$_{1-7}$alkyl (e.g., —(CH$_2$)$_w$—COON, w is 1, 2, 3, or 4);

acyl-C$_{1-7}$alkyl (e.g., —(CH$_2$)$_w$-acyl, w is 1, 2, 3, or 4);

hydroxy-C$_{1-7}$alkyl (e.g., —(CH$_2$)$_w$—OH, w is 1, 2, 3, or 4);

C$_{1-7}$alkoxy-C$_{1-7}$alkyl (e.g., —(CH$_2$)$_w$—O—C$_{1-7}$alkyl, w is 1, 2, 3, or 4).

In one embodiment, each of the substituents (e.g., on A, Q$^1$, R$^N$, Q$^2$) (e.g., R$^4$), if present, is independently selected from:

(1) —C(=O)OH;

(2) —C(=O)OMe, —C(=O)OEt, —C(=O)O(iPr), —C(=O)O(tBu); —C(=O)O(cPr); —C(=O)OCH$_2$CH$_2$OH, —C(=O)OCH$_2$CH$_2$OMe, —C(=O)OCH$_2$CH$_2$OEt; —C(=O)OPh, —C(=O)OCH$_2$Ph;

(3) —(C=O)NH$_2$, —(C=O)NMe$_2$, —(C=O)NEt$_2$, —(C=O)N(iPr)$_2$, —(C=O)N(CH$_2$CH$_2$OH)$_2$; —(C=O)— morpholino, —(C=O)NHPh, —(C=O)NHCH$_2$Ph;

(4) —C(=O)H, —(C=O)Me, —(C=O)Et, —(C=O)(tBu), —(C=O)-cHex, —(C=O)Ph; —(C=O)CH$_2$Ph;

(5) —F, —Cl, —Br, —I;

(6) —CN;

(7) —NO$_2$;

(8) —OH;

(9) —OMe, —OEt, —O(iPr), —O(tBu), —OPh, —OCH$_2$Ph;
—OCF$_3$, —OCH$_2$CF$_3$;
—OCH$_2$CH$_2$OH, —OCH$_2$CH$_2$OMe, —OCH$_2$CH$_2$OEt;
—OCH$_2$CH$_2$NH$_2$, —OCH$_2$CH$_2$NMe$_2$, —OCH$_2$CH$_2$N(iPr)$_2$;
—OPh-Me, —OPh-OH, —OPh-OMe, —OPh-F, —OPh-Cl, —OPh-Br, —OPh-I;

(10) —SH;

(11) —SMe, —SEt, —SPh, —SCH$_2$Ph;

(12) —OC(=O)Me, —OC(=O)Et, —OC(=O)(iPr), —OC(=O)(tBu); —OC(=O)(cPr); —OC(=O)CH$_2$CH$_2$OH, —OC(=O)CH$_2$CH$_2$OMe, —OC(=O)CH$_2$CH$_2$OEt; —OC(=O)Ph, —OC(=O)CH$_2$Ph;

(13) —OC(=O)NH$_2$, —OC(=O)NHMe, —OC(=O)NMe$_2$, —OC(=O)NHEt, —OC(=O)NEt$_2$, —OC(=O)NHPh, —OC(=O)NCH$_2$Ph;

(14) —NH$_2$, —NHMe, —NHEt, —NH(iPr), —NMe$_2$, —NEt$_2$, —N(iPr)$_2$, —N(CH$_2$CH$_2$OH)$_2$; —NHPh, —NHCH$_2$Ph; piperidino, piperazino, morpholino;

(15) —NH(C=O)Me, —NH(C=O)Et, —NH(C=O)nPr, —NH(C=O)Ph, —NHC(=O)CH$_2$Ph; —NMe(C=O)Me, —NMe(C=O)Et, —NMe(C=O)Ph, —NMeC(=O)CH$_2$Ph;

(16) —NH(C=O)NH$_2$, —NH(C=O)NHMe, —NH(C=O)NHEt, —NH(C=O)NPh, —NH(C=O)NHCH$_2$Ph; —NH(C=S)NH$_2$, —NH(C=S)NHMe, —NH(C=S)NHEt, —NH(C=S)NPh, —NH(C=S)NHCH$_2$Ph;

(17) —NHSO$_2$Me, —NHSO$_2$Et, —NHSO$_2$Ph, —NHSO$_2$PhMe, —NHSO$_2$CH$_2$Ph; —NMeSO$_2$Me, —NMeSO$_2$Et, —NMeSO$_2$Ph, —NMeSO$_2$PhMe, —NMeSO$_2$CH$_2$Ph;

(18) —SO$_2$Me, —SO$_2$CF$_3$, —SO$_2$Et, —SO$_2$Ph, —SO$_2$PhMe, —SO$_2$CH$_2$Ph;

(19) —OSO$_2$Me, —OSO$_2$CF$_3$, —OSO$_2$Et, —OSO$_2$Ph, —OSO$_2$PhMe, —OSO$_2$CH$_2$Ph;

(20) —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph;

(21) =O;

(22) =NH, =NMe, =NEt;

(23) =NOH, =NOMe, =NOEt, =NO(nPr), =NO(iPr), =NO(cPr), =NO(CH$_2$-cPr);

(24) —CH$_2$Ph, —CH$_2$Ph-Me, —CH$_2$Ph-OH, —CH$_2$Ph-F, —CH$_2$Ph-Cl;

(25) -Ph, -Ph-Me, -Ph-OH, -Ph-OMe, -Ph-NH$_2$, -Ph-F, -Ph-Cl, -Ph-Br, -Ph-I; pyridyl, pyrazinyl, pyrimidinyl, pyridazinyl, furanyl, thiophenyl, pyrrolyl, imidazolyl, pyrazolyl, oxazolyl, thiazolyl, thiadiazolyl;

(26) pyrrolidinyl, imidazolidinyl, pyrazolidinyl, piperidinyl, piperazinyl, azepinyl, tetrahydrofuranyl, tetrahydropyranyl, morpholinyl, azetidinyl;

(27) -Me, -Et, -nPr, -iPr, -nBu, -iBu, -sBu, -tBu, -nPe; -cPr, -cHex; —CH=CH$_2$, —CH$_2$—CH=CH$_2$;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—CH$_2$OH, —CH$_2$OMe, —CH$_2$OEt, —CH$_2$NH$_2$, —CH$_2$NMe$_2$;
—CH$_2$CH$_2$OH, —CH$_2$CH$_2$OMe, —CH$_2$CH$_2$OEt, —CH$_2$CH$_2$NH$_2$, —CH$_2$CH$_2$NMe$_2$;

(28) —O—CH$_2$—O—, —O—CH$_2$—CH$_2$—O—, —O—CH$_2$—CH$_2$—CH$_2$—O—, —O—CF$_2$—O—, and —O—CF$_2$—CF$_2$—O—.

The HDACi: Some Preferred Examples

All plausible combinations of the embodiments described above are explicitly disclosed herein, as if each combination was individually and explicitly recited.

In one preferred embodiment, the HDACi is selected from compounds of the following formula:

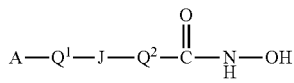

wherein:
A is independently:
 phenyl,
 and is unsubstituted or substituted;
$Q^1$ is independently:
 a covalent bond,
 —$CH_2$—,
 —$CH_2CH_2$—,
 —CH=CH—;
J is independently:
 —$NR^N$—S(=O)$_2$—, or
 —S(=O)$_2$—$NR^N$—;
$R^N$ is independently:
 —H, or
 $C_{1-4}$alkyl,
 and is unsubstituted;
$Q^2$ is independently:
 phenylene-$C_{1-4}$alkylene,
 phenylene-$C_{2-4}$alkenylene,
 and is unsubstituted;
and pharmaceutically acceptable salts, solvates, amides, esters, ethers, chemically protected forms, and prodrugs thereof.

In one embodiment, the HDACi is selected from compounds of the following formulae, and substituted analogs thereof (e.g., where the terminal phenyl group is substituted, where the sulfonamide nitrogen is substituted, etc., e.g., with one or more substituents as defined above under the heading "The HDACi: Substituents"), and pharmaceutically acceptable salts, solvates, amides, esters, ethers, chemically protected forms, and prodrugs thereof:

1.

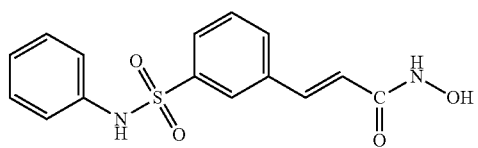

2.

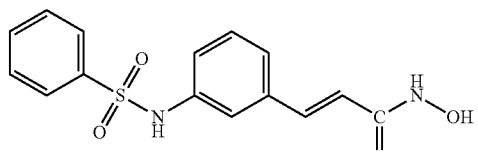

3.

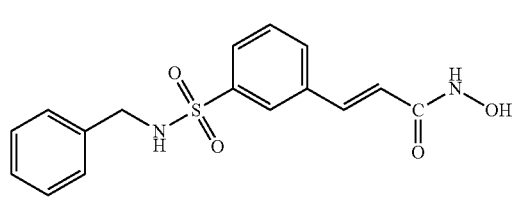

4.

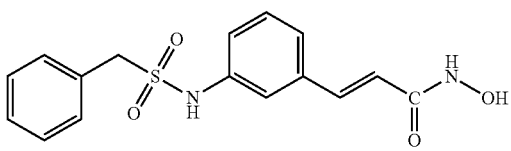

5.

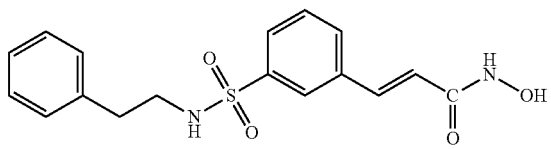

6.

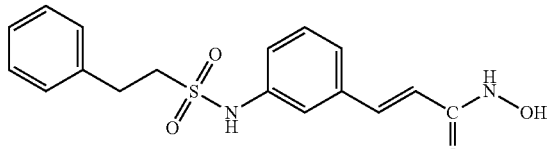

7.

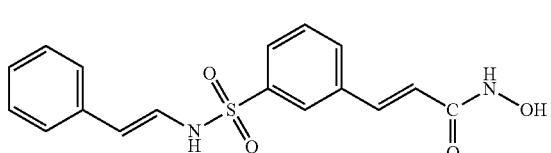

8.

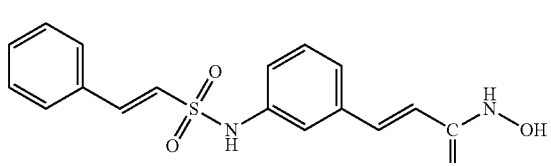

In one embodiment, the HDACi is selected from compounds of the following formula, and substituted analogs thereof (e.g., where the terminal phenyl group is substituted, where the sulfonamide nitrogen is substituted, etc., e.g., with one or more substituents as defined above under the heading "The HDACi: Substituents"), and pharmaceutically acceptable salts, solvates, amides, esters, ethers, chemically protected forms, and prodrugs thereof:

PXD-101

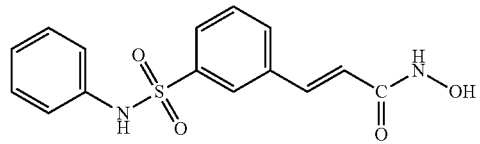

In one embodiment, the HDACi is selected from the following compound, and pharmaceutically acceptable salts, solvates, amides, esters, ethers, chemically protected forms, and prodrugs thereof:

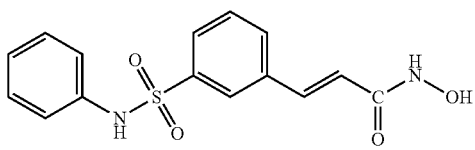

PXD-101

The HDACi: Other Forms

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

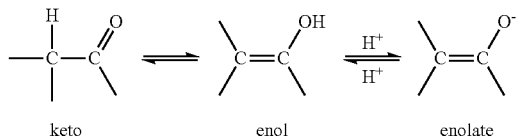

keto       enol       enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the known methods, in a known manner.

Unless otherwise specified, a reference to a particular compound also includes ionic, salt, solvate, protected forms thereof, and prodrugs thereof, for example, as discussed below.

It may be convenient or desirable to prepare, purify, and/or handle a corresponding salt of the active compound, for example, a pharmaceutically acceptable salt. Examples of pharmaceutically acceptable salts are discussed in Berge et al., 1977, "Pharmaceutically Acceptable Salts," J. Pharm. Sci., Vol. 66, pp. 1-19.

For example, if the compound is anionic, or has a functional group that may be anionic (e.g., —COOH may be —COO$^−$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). A wide variety of such "protecting," "blocking," or "masking" methods are widely used and well known in organic synthesis.

It may be convenient or desirable to prepare, purify, and/or handle the active compound in the form of a proHDACi. The term "proHDACi," as used herein, pertains to a compound which, when metabolised (e.g., in vivo), yields the desired active compound. Typically, the proHDACi is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(=O) OR) is cleaved to yield the active HDACi. Such esters may be formed by esterification, for example, of any of the carboxylic acid groups (—C(=O)OH) in the parent compound, with, where appropriate, prior protection of any other reactive groups present in the parent compound, followed by deprotection if required.

Cyclodextrin

The term "cyclodextrin", as used herein (e.g., in connection with component (b)), relates to both cyclodextrins per se, and cyclodextrin derivatives, including, for example, the cyclodextrin derivatives described herein.

Cyclodextrins, also known as cyclomyloses, cycloglucans, and Schardinger dextrins, are naturally occurring clathrates obtained, for example, from the action of *Bacillus macerans* amylase on starch to form homogenous cyclic α-(1→4) linked glucopyranose units. α-, β-, and γ-cyclodextrins are composed of six, seven, and eight units, respectively, and have molecular weights of 972.84, 1134.98, and 1297.12 g/mol, respectively. Cyclodextrins have hydrophobic cavities and form inclusion compounds with organic substance, salts, and halogens in the solid state or in aqueous solutions. They are used as complexing agents, and in the study of enzyme action. To date, cyclodextrins have only been used in a limited number of small volume parenteral formulations. See, for example, Loftsson, T., 1998, "Cyclodextrins in Pharmaceutical Formulations," Report for Nordic Industrial Fund); and Strickley, R., 2004, "Solubilising Excipients in Oral and Injectable Formulations", Pharm. Res., Vol. 21, No. 2, pp. 201-230.

A range of cyclodextrin derivatives are known, for example, where one or more of the primary and/or secondary pendant hydroxy (—OH) groups have been derivatised, for example, to form ether groups (e.g., dimethyl ether; hydroxyethyl ether; 2-hydroxypropyl ether; carboxymethyl ether; carboxyethyl ether; glucosyl ether; maltosyl ether; sulfobutyl ether). Molar substitution ratios of, for example, 0.6, 0.8, and 1.0 (e.g., 0.5-1.0) are common.

In one embodiment, the cyclodextrin is selected from: α-cyclodextrin; β-cyclodextrin; γ-cyclodextrin; ($C_{1-4}$alkyl)-α-cyclodextrin; ($C_{1-4}$alkyl)-β-cyclodextrin; ($C_{1-4}$alkyl)-γ-cyclodextrin; (hydroxy-$C_{1-4}$alkyl)-α-cyclodextrin; (hydroxy-$C_{1-4}$alkyl)-β-cyclodextrin; (hydroxy-$C_{1-4}$alkyl)-γ-cyclodextrin; (carboxy-$C_{1-4}$alkyl)-α-cyclodextrin; (carboxy-$C_{1-4}$alkyl)-β-cyclodextrin; (carboxy-$C_{1-4}$alkyl)-γ-cyclodextrin; saccharide ethers of α-cyclodextrin; saccharide ethers of β-cyclodextrin; saccharide ethers of γ-cyclodextrin; and sulfobutyl ethers of α-cyclodextrin, β-cyclodextrin, or γ-cyclodextrin.

Examples of $C_{1-4}$alkyl groups, in this context, include -Me, -Et, -nPr, -iPr, and -cPr.

Examples of saccharide ethers, in this context, include glucosyl and maltosyl ethers.

An especially preferred cyclodextrin is: hydroxypropyl-β-cyclodextrin.

Preferably, the cyclodextrin has a purity of pharmaceutical grade or equivalent.

The following cyclodextrins and cyclodextrin derivatives may be obtained, for example, from Wacker-Chemie GmbH, Munich, Germany:
α-cyclodextrin (Cavamax® W6 pharma);
γ-cyclodextrin (Cavamax® W8 pharma);
Hydroxypropyl-α-cyclodextrin (Cavasol® W6 HP TL);
Hydroxypropyl-β-cyclodextrin (Cavasol® W7 HP pharma);
Hydroxypropyl-γ-cyclodextrin (Cavasol® W8 HP pharma).

Without wishing to be bound to any particular theory, the inventors believe that the terminal phenyl group of PXD-101 (or the optionally substituted terminal phenyl group of analogs of PXD-101) forms a complex with cyclodextrin, such as hydroxypropyl-β-cyclodextrin.

Arginine

Arginine, also known as L-arginine, 2-amino-5-guanidinovaleric acid, and (S)-2-amino-5-[(aminoiminomethyl)-aminolpentanoic acid, has a molecular weight of 174.20. It is soluble in water (a saturated aqueous solution contains 15% w/w at 21° C.) and is alkaline in nature (but less alkaline than meglumine). It is often provided as an acid addition salt, for example, as the hydrochloride salt. Arginine is well tolerated in humans at doses up to 30 g/kg, for example, when given as a nutritional additive.

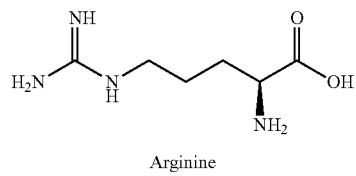 [SMILES: N=C(N)NCCC[C@H](N)C(=O)O]

Arginine

In one embodiment, the arginine is free arginine or a pharmaceutically acceptable salt of arginine.

Preferably, the arginine is L-arginine.

In one embodiment, the arginine is free L-arginine or a pharmaceutically acceptable salt of L-arginine.

Preferably, the arginine has a purity of pharmaceutical grade or equivalent.

L-arginine for HDACi formulation (conforming to both European and United States standards) may be obtained, for example, from Ajinomoto, Kanagawa, Japan (Catalog No. 2).

Without wishing to be bound to any particular theory, the inventors believe that the acrylamide and/or sulphonamide groups of PXD-101 (and analogs thereof) are take part in in situ salt formation with arginine (and meglumine, discussed below), and so give rise to enhanced solubility.

Meglumine

Meglumine, also known as N-methylglucamine, 1-deoxy-1-(methylamino)-D-glucitol, and N-methyl-D-glucamine, has a molecular weight of 195.21 g/mol and a melting point of about 129-131° C. It is soluble in water (~100 g in 100 mL at 25° C.) and is alkaline in nature (and is more alkaline than arginine) (pH~10.5 for a 1 wt % aqueous solution). It forms salts with acids and complexes with metals, and is used in many pharmaceutical formulations.

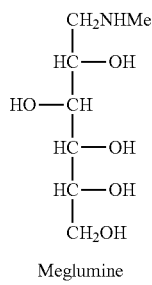

Meglumine

In one embodiment, the meglumine is free meglumine or a pharmaceutically acceptable salt of meglumine.

Preferably, the meglumine has a purity of pharmaceutical grade or equivalent.

Meglumine for HDACi formulation (conforming to both European and United States standards) may be obtained, for example, from Merck KgaA, Germany.

Other Additional Ingredients

In one embodiment, the pharmaceutical composition further comprises one or more other additional pharmaceutically acceptable ingredients (e.g., pharmaceutically acceptable carriers, etc.)

In one embodiment, the pharmaceutical composition additionally comprises one or more other pharmaceutically acceptable ingredients well known to those skilled in the art, including, but not limited to, pharmaceutically acceptable carriers, diluents, excipients, adjuvants, buffers, pH modifiers, preservatives, anti-oxidants, bacteriostats, stabilisers, suspending agents, solubilisers, surfactants (e.g., wetting agents), colouring agents, and isotonicizing solutes (i.e., which render the formulation isotonic with the blood, or other relevant bodily fluid, of the intended recipient). Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, N.Y., USA), *Remington's Pharmaceutical Sciences*, 18th edition, Mack Publishing Company, Easton, Pa., 1990; and *Handbook of Pharmaceutical Excipients*, 2nd edition, 1994.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive undesired toxicity, irritation, allergic response, or other problem or complication, commensurate with a reasonable benefit/risk ratio. Each carrier, diluent, excipient, etc. must also be "acceptable" in the sense of being compatible with the other ingredients of the composition.

In one embodiment, the composition further comprises other active agents, for example, other therapeutic or prophylactic agents.

Format

As used herein, the term "formulation" describes a material that is in a form (e.g., a liquid) that is ready for administration, whereas the term "pre-formulation" describes a material (e.g., lyophilate/lyophilisate, concentrate, etc.) from which a formulation may be prepared (e.g., by re-hydration, dilution, etc.).

In one embodiment, the composition (e.g., formulation, pre-formulation) is a liquid (e.g., at room temperature, i.e., 25° C. and standard atmospheric pressure, i.e., 1.01325 bar).

The liquid composition (e.g., formulation, pre-formulation) may be a solution, a suspension, an emulsion, etc., in which the HDACi and other components (e.g., cyclodextrin, arginine, meglumine, etc.) are dissolved, suspended, or otherwise provided (e.g., in a liposome or other microparticulate).

In one embodiment, the composition (e.g., formulation, pre-formulation) is an aqueous liquid (e.g., comprising at least 30% w/w water, e.g., at least 50% w/w water, at least 70% w/w water).

In one embodiment, the composition (e.g., formulation, pre-formulation) is an aqueous isotonic liquid (e.g., isotonic with blood).

In one embodiment, the composition (e.g., formulation, pre-formulation) is sterile and pyrogen-free (i.e., free of pyrogens).

In one embodiment, the composition (e.g., pre-formulation) is a liquid concentrate from which a formulation may be prepared, for example, by dilution.

In one embodiment, the composition (e.g., pre-formulation) is a solid (e.g., at room temperature, i.e., 25° C. and standard atmospheric pressure, i.e., 1.01325 bar) (e.g., powder, granules, tablets, lyophilates/lyophilisates, etc.), from which a formulation may be prepared, for example, by hydration (or re-hydration), optionally followed by further dilution.

Materials suitable for dilution, hydration, and/or re-hydration include, for example, water-for-injection, aqueous saline solution (e.g. 0.9% w/v NaCl), aqueous glucose solution e.g., 5% w/v glucose BP), saline for injection/infusion, glucose for injection/infusion, Ringer's solution, lactated Ringer's solution, etc.

Suitable saline solution ("saline for infusion", 0.9% w/v sodium chloride BP) may be obtained, for example, from Baxter Healthcare Ltd, Thetford, Norfolk, UK (Product Code FUE1322).

Suitable glucose solution ("glucose for infusion", 5% w/v glucose BP) may be obtained, for example, from Baxter Healthcare Ltd, Thetford, Norfolk, UK (Product Code FUE1322).

The pharmaceutical compositions (e.g., formulations, pre-formulations) may be presented in unit-dose or multi-dose sealed containers, for example, ampoules and vials.

The pharmaceutical formulation may be prepared, e.g., from a pre-formulation, extemporaneously, e.g., immediately prior to use, for example, in an intravenous (I.V.) infusion bag.

One aspect of the present in invention pertains to a pharmaceutical composition (e.g., formulation, pre-formulation), as described herein, in a suitable container (e.g., vial, ampoule, intravenous (I.V.) infusion bag).

One aspect of the present in invention pertains to a vial or ampoule containing a pharmaceutical composition (e.g., formulation, pre-formulation), as described herein.

One aspect of the present in invention pertains to a vial or ampoule containing a pharmaceutical pre-formulation (e.g., a liquid concentrate), as described herein.

One aspect of the present in invention pertains to an intravenous (I.V.) infusion bag containing a pharmaceutical composition (e.g., formulation), as described herein.

Amount of HDACi

The pharmaceutical formulation comprises a therapeutically-effective amount of HDACi.

The pharmaceutical composition comprises an amount of HDACi so that, upon subsequent formation of a pharmaceutical formulation from said pharmaceutical composition (e.g., by dilution, hydration, re-hydration, etc.), said pharmaceutical formulation comprises a therapeutically-effective amount of HDACi.

It will be appreciated by one of skill in the art that appropriate dosages of the HDACi (and concentrations of HDACi in formulations and compositions) can vary from subject to subject. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other HDACis, compounds, and/or materials used in combination with the HDACi, the severity of the condition, and the species, sex, age, weight, condition, general health, and prior medical history of the subject. The amount of HDACi and route of administration will ultimately be at the discretion of the physician, veterinarian, or clinician, although generally the dosage will be selected to achieve local concentrations at the site of action that achieve the desired effect without causing substantial harmful or deleterious side-effects.

An example of a preferred dosage is 150 µmol/kg. For a HDACi (e.g., PXD-101) with a molecular weight of 318 g/mol, that is ~47.7 mg/kg. For a 70 kg subject, that is ~3.3 g. When diluted in a 1.0 L intravenous bag, that is a formulation concentration of ~3.3 g/L (~3.3 mg/mL) or ~10 mM. A suitable liquid concentrate (e.g., pre-formulation) may have a concentration of 10-100 times greater than the desired formulation, and so have a concentration of ~33-330 g/L (~33-330 mg/mL, e.g., ~50 mg/mL), or ~0.1-1.0 M.

In one embodiment, the composition (e.g., formulation) has a HDACi concentration of at least 0.01, 0.02, 0.05, 0.1, 0.2, 0.5, 1.0, 2.0, or 5.0 mg/mL.

In one embodiment, the composition (e.g., formulation) has a HDACi concentration of up to and including 200, 100, 50, 20, 10, 5, 2, 1, 0.5, or 0.2 mg/mL.

In one embodiment, the HDACi concentration is 0.1-10 mg/mL. In one embodiment, the HDACi concentration is 0.5-10 mg/mL. In one embodiment, the HDACi concentration is 1.0-10 mg/mL. In one embodiment, the HDACi concentration is 0.1-5 mg/mL. In one embodiment, the HDACi concentration is 0.5-5 mg/mL. In one embodiment, the HDACi concentration is 1.0-5 mg/mL. In one embodiment, the composition (e.g., formulation) has a HDACi concentration of at least 0.01, 0.03, 0.05, 0.1, 0.3, 0.5, 1.0, 3.0, 5.0, or 10 mM. In one embodiment, the composition (e.g., formulation) has a HDACi concentration of up to and including 300, 200, 100, 50, 30, 20, 15, 10, 5, 3, 1, 0.5, or 0.3 mM.

In one embodiment, the HDACi concentration is 0.3-30 mM. In one embodiment, the HDACi concentration is 1.0-30 mM. In one embodiment, the HDACi concentration is 2.0-30 mM. In one embodiment, the HDACi concentration is 3.0-30 mM. In one embodiment, the HDACi concentration is 0.3-15 mM. In one embodiment, the HDACi concentration is 1.0-15 mM. In one embodiment, the HDACi concentration is 2.0-15 mM. In one embodiment, the HDACi concentration is 3.0-15 mM.

The composition (e.g., pre-formulation) may have a HDACi concentration that is, for example, 1-1000 times greater than the HDACi concentration of the corresponding formulation.

In one embodiment, the composition (e.g., pre-formulation) has a HDACi concentration of at least 1, 2, 5, 10, 20, 50, or 100 times greater. In one embodiment, the composition (e.g., pre-formulation) has a HDACi concentration of up to and including 1000, 500, 200, 100, 50, 20, 10, 5, or 2 times greater.

In one embodiment, the HDACi concentration is 10-500 times greater. In one embodiment, the HDACi concentration is 10-200 times greater. In one embodiment, the HDACi concentration is 10-100 times greater. In one embodiment, the HDACi concentration is 10-50 times greater. In one embodiment, the HDACi concentration is 10-20 times greater.

For example, in one embodiment, the composition (e.g., pre-formulation) has a HDACi concentration of 30-600 mM (corresponding to 10-20 times 3.0-30 mM).

In one embodiment, the composition (e.g., pre-formulation) has a HDACi concentration of at least 0.1, 0.2, 0.5, 1.0, 2.0, 5.0, 10, 20, 30, or 50 mg/mL. In one embodiment, the composition (e.g., pre-formulation) has a HDACi concentration of up to and including 1000, 500, 300, 200, 100, 50, 20, 10, 5, or 2 mg/mL.

In one embodiment, the HDACi concentration is 5-500 mg/mL. In one embodiment, the HDACi concentration is 10-500 mg/mL. In one embodiment, the HDACi concentration is 20-500 mg/mL. In one embodiment, the HDACi concentration is 30-500 mg/mL. In one embodiment, the HDACi concentration is 5-300 mg/mL. In one embodiment, the HDACi concentration is 10-300 mg/mL. In one embodiment, the HDACi concentration is 20-300 mg/mL. In one embodiment, the HDACi concentration is 30-300 mg/mL. In one embodiment, the HDACi concentration is ~50 mg/mL.

In one embodiment, the composition (e.g., pre-formulation) has a HDACi concentration of at least 0.3, 0.5, 1.0, 1.5, 2.0, 3.0, 5.0, 10, 30, 50, 100 mM. In one embodiment, the composition (e.g., pre-formulation) has a HDACi concentration of up to and including 3000, 1000, 500, 300, 100, 50, 30, 20, 15, 10, 5, or 3 mM.

In one embodiment, the HDACi concentration is 10-1000 mM. In one embodiment, the HDACi concentration is 30-1000 mM. In one embodiment, the HDACi concentration is 50-1000 mM. In one embodiment, the HDACi concentration is 100-1000 mM. In one embodiment, the HDACi concentration is 10-500 mM. In one embodiment, the HDACi concentration is 30-500 mM. In one embodiment, the HDACi concentration is 50-500 mM. In one embodiment, the HDACi concentration is 100-500 mM.

Where the HDACi is provided in the form of a salt, the amount is calculated on the basis of the parent compound. Consequently, the above values (e.g., 30-300 mg/mL, ~50 mg/mL) pertain to the parent compound, and not, for example, a salt thereof.

Amount of Cyclodextrin

In one embodiment, if cyclodextrin is present, the molar ratio of cyclodextrin to HDACi is at least 0.5, 0.7, 0.8, 0.9, 1.0, 1.1, 1.2, 1.3, 1.4, or 1.5.

In one embodiment, if cyclodextrin is present, the molar ratio of cyclodextrin to HDACi is up to and including 5, 4, 3.5, 3, 2.5, 2.0, 1.9, 1.8, 1.7, 1.6, or 1.5.

In one embodiment, the molar ratio is 0.5-5. In one embodiment, the molar ratio is 0.8-4. In one embodiment, the molar ratio is 1-3. In one embodiment, the molar ratio is 1.2-2.5. In one embodiment, the molar ratio is 1.4-2. In one embodiment, the molar ratio is 1.5-1.9

An example of a preferred HDACi concentration for a composition (e.g, pre-formulation, formulation) is ~10 mM. If that composition (e.g, pre-formulation, formulation) is to have a cyclodextrin to HDACi molar ratio of ~1.5-1.9, that corresponds to a cyclodextrin concentration of ~15-19 mM.

An example of a preferred HDACi is PXD-101, which has a molecular weight of ~318 g/mol. β-cyclodextrin has a molecular weight of ~1135 g/mol. The cyclodextrin to HDACi molecular weight ratio is ~1135/318 or ~3.57. If the composition (e.g, pre-formulation, formulation) is to have a cyclodextrin to HDACi molar ratio of ~1.5-1.9, that corresponds to a cyclodextrin to HDACi weight ratio of ~5.3-6.8 (i.e., 5.3-6.8 grams of β-cyclodextrin for each gram of PXD-101).

It may be preferred to ensure a total cyclodextrin dose of less than 5000, 2000, 1000, 500, 400, 300, 200, 100, or 50 mg/kg.

Amount of Arginine

In one embodiment, if arginine is present, the molar ratio of arginine to HDACi is at least 0.5, 0.7, 0.8, 0.9, 1.0, 1.1, 1.2, 1.3, 1.4, or 1.5.

In one embodiment, if arginine is present, the molar ratio of arginine to HDACi is up to and including 5, 4, 3.5, 3, 2.5, 2.0, 1.9, 1.8, 1.7, 1.6, or 1.5.

In one embodiment, the molar ratio is 0.5-5. In one embodiment, the molar ratio is 0.8-4. In one embodiment, the molar ratio is 1-3. In one embodiment, the molar ratio is 1.2-2.5. In one embodiment, the molar ratio is 1.4-2. In one embodiment, the molar ratio is 1.5-1.9

An example of a preferred HDACi concentration for a composition (e.g., formulation) is ~10 mM. If that composition (e.g., formulation) is to have an arginine to HDACi molar ratio of ~1.5-1.9, that corresponds to an arginine concentration of ~15-19 mM.

An example of a preferred HDACi is PXD-101, which has a molecular weight of ~318 g/mol. Free arginine has a molecular weight of ~174 g/mol. The arginine to HDACi molecular weight ratio is ~174/318 or ~0.547. If the composition (e.g., pre-formulation, formulation) is to have an arginine to HDACi molar ratio of ~1.5-1.9, that corresponds to an arginine to HDACi weight ratio of ~0.82-1.04 (i.e., 0.82-1.04 grams of arginine for each gram of PXD-101).

It may be preferred to ensure a total arginine dose of less than 200, 100, 50, 30, or 20 g/kg.

Amount of Meglumine

In one embodiment, if meglumine is present, the molar ratio of meglumine to HDACi is at least 0.5, 0.7, 0.8, 0.9, 1.0, 1.1, 1.2, 1.3, 1.4, or 1.5.

In one embodiment, if meglumine is present, the molar ratio of meglumine to HDACi is up to and including 5, 4, 3.5, 3, 2.5, 2.0, 1.9, 1.8, 1.7, 1.6, or 1.5.

In one embodiment, the molar ratio is 0.5-5. In one embodiment, the molar ratio is 0.8-4. In one embodiment, the molar ratio is 1-3. In one embodiment, the molar ratio is 1.2-2.5. In one embodiment, the molar ratio is 1.4-2. In one embodiment, the molar ratio is 1.5-1.9

An example of a preferred HDACi concentration for a composition (e.g., formulation) is ~10 mM. If that composition (e.g., formulation) is to have a meglumine to HDACi molar ratio of ~1.5-1.9, that corresponds to a meglumine concentration of ~15-19 mM.

An example of a preferred HDACi is PXD-101, which has a molecular weight of ~318 g/mol. Free meglumine has a molecular weight of ~195 g/mol. The meglumine to HDACi molecular weight ratio is ~195/318 or ~0.613. If the composition (e.g., pre-formulation, formulation) is to have a meglumine to HDACi molar ratio of ~1.5-1.9, that corresponds to a meglumine to HDACi weight ratio of ~0.92-1.17 (i.e., 0.92-1.17 grams of meglumine for each gram of PXD-101).

It may be preferred to ensure a total meglumine dose of less than 200, 100, 50, 30, or 20 g/kg.

Preparation of Compositions

The compositions (e.g., pre-formulations, formulations) may be prepared using conventional methods that are well known in the field of pharmacy. For example, methods that use standard laboratory or pharmaceutical processing equipment are well known to those in the field of pharmacy.

One aspect of the present invention pertains to a method of preparing a composition (e.g., pre-formulation, formulation) (as described herein) by combining: (a) a HDACi as defined herein, and (b) one or more of the following additional ingredients: cyclodextrin, arginine, and meglumine; and optionally one or more other additional pharmaceutically acceptable ingredients (as described herein).

For example an appropriate amount of pure, dry HDACi (e.g., PXD-101) may be dissolved in a solution of salt former (e.g., arginine, meglumine) or cyclodextrin in water at a suitable concentration as described herein. Solubilisation may be achieved over a period of from about 1 minute to about 1 hour by stirring, for example, using a magnetic stirrer, paddle stirrer, or turbine mixer, with or without the application of heat. The resulting solution is then diluted to the final volume, e.g., with the appropriate grade of water, and stirred for a further period of time until the solution is homogenous.

If necessary, the pH of the solution can be adjusted using a suitable acid (e.g., HCl) to achieve a pH of greater than or equal to about 8.5. However, there may be a risk of precipitating the HDACi if the pH is adjusted.

The solution is passed through a suitable filter (e.g., sterilising grade 0.2 μm filter) and placed in appropriate containers (e.g., vials, ampoules, etc.) in a suitable pharmaceutical manufacturing environment, and sealed/capped.

Optionally, a lyophilisate is prepared by placing the solution in vials fitted with a suitable lyophilisation stopper and removing the water by freeze-drying to provide a powder suitable for reconstitution/re-hydration using a suitable re-hydration medium (e.g., saline, glucose, etc.). After freeze-drying, the vials are sealed and capped.

One aspect of the present invention pertains to a method of preparing a formulation (as described herein) by diluting, reconstituting, hydrating, re-hydrating, etc. a pre-formulation (as described herein).

One aspect of the present invention pertains to a pharmaceutical composition (e.g., formulation) (as described herein) obtained by diluting, reconstituting, hydrating, re-hydrating, etc. a pre-formulation (as described herein).

One aspect of the present invention pertains to a pharmaceutical composition (e.g., formulation) (as described herein) obtainable by diluting, reconstituting, hydrating, re-hydrating, etc. a pre-formulation (as described herein).

For example, formulations may be prepared from pre-formulations, for example, extemporaneously, by dilution, reconstitution, hydration, re-hydration, etc., using appropriate liquids, e.g., water (e.g., water-for-injection), aqueous saline (e.g., 0.9% w/v saline solution), aqueous glucose (e.g., 5% w/v glucose solution), etc.

For example, an appropriate amount of liquid concentrated composition (e.g., pre-formulation) (initially provided in a vial or ampoule) may be introduced into a typical 1 L intravenous saline or glucose bag, and the resulting formulation used for administration by intravenous infusion.

For example, an appropriate amount of a lyophilate/lyophilisate composition (e.g., pre-formulation) may be reconstituted (or re-hydrated) by adding a suitable aqueous medium (e.g., water for injection, 0.9% saline solution, 5% glucose solution, etc.), e.g., to the vial containing the lyophilate/lyophilisate, e.g., using a suitable syringe and needle. The contents of the vial may then be shaken to dissolve the lyophilised powder. The resulting composition may then be used as a formulation, and administered to the subject, or may be used as a pre-formulation, and diluted to the required concentration, e.g., by addition to a suitable infusion medium, e.g., in an infusion bag.

One aspect of the present invention pertains to a method of formulating a HDACi (as described herein) comprising the step of: combining said HDACi with one or more of the following additional ingredients: cyclodextrin, arginine, and meglumine (as described herein); and optionally one or more other additional pharmaceutically acceptable ingredients (as described herein).

One aspect of the present invention pertains to a method of increasing the concentration of a HDACi (as described herein) in a pharmaceutical composition, comprising the step of: formulating said HDACi with one or more of the following additional ingredients: cyclodextrin, arginine, and meglumine (as described herein); and optionally one or more other additional pharmaceutically acceptable ingredients (as described herein).

Solid Forms

One aspect of the present invention pertains to a pharmaceutical composition comprising an HDAC inhibitor (e.g., PXD-101) in solid dosage form (e.g., tablet, capsule, gelatin tablet, etc.) (e.g., a gelatine capsule).

One aspect of the present invention pertains to a solid dosage form (e.g., tablet, capsule, gelatin tablet, etc.) (e.g., a gelatine capsule) containing an HDAC inhibitor, as described herein.

One aspect of the present invention pertains to a solid dosage form (e.g., tablet, capsule, gelatin tablet, etc.) (e.g., a gelatine capsule) containing a pharmaceutical composition (e.g., formulation), as described herein.

Medical Use, Methods of Treatment, Etc.

One aspect of the present invention pertains to the pharmaceutical composition components as described herein (e.g., a HDACi; one or more of cyclodextrin, arginine, and meglumine; etc.) for use in a method of treatment of the human or animal body by therapy.

One aspect of the present invention pertains to a pharmaceutical composition (e.g., pre-formulation, formulation), as described herein, for use in a method of treatment of the human or animal body by therapy.

One aspect of the present invention pertains to use of the pharmaceutical composition components as described herein (e.g., a HDACi; one or more of cyclodextrin, arginine, and meglumine; etc.) in the manufacture of a medicament for the treatment of a condition, as described herein.

One aspect of the present invention pertains to use of a pharmaceutical composition (e.g., pre-formulation), as described herein, in the manufacture of a medicament for the treatment of a condition, as described herein.

One aspect of the present invention pertains to a method of treatment, comprising administering to a subject in need of treatment a pharmaceutical composition (e.g., formulation), as described herein.

One aspect of the present invention pertains to a method of (a) regulating (e.g., inhibiting) cell proliferation; (b) inhibiting cell cycle progression; (c) promoting apoptosis; or (d) a combination of one or more of these, in vitro or in vivo, comprising contacting a cell with a pharmaceutical composition (e.g., formulation) as described herein.

Any type of cell may be treated, including but not limited to, lung, gastrointestinal (including, e.g., bowel, colon, colorectal), breast (mammary), ovarian, prostate, liver (hepatic), kidney (renal), bladder, pancreas, brain, and skin.

One aspect of the present invention pertains to a method of administering a HDACi, as defined herein, to a subject, comprising administering to said subject a pharmaceutical composition (e.g., formulation), as described herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included. For example, use with subjects who have not yet developed the condition, but who are at risk of developing the condition, is encompassed by the term "treatment."

The term "therapeutically-effective amount," as used herein, pertains to that amount of HDACi that is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. For example, the compounds described herein may also be used in combination therapies, e.g., in conjunction with other agents, for example, cytotoxic agents, etc. Examples of treatments and therapies include, but are not limited to, chemotherapy (the administration of active agents, including, e.g., HDACis, antibodies (e.g., as in immunotherapy), prodrugs (e.g., as in photodynamic therapy, GDEPT, ADEPT, etc.); surgery; radiation therapy; and gene therapy.

Conditions

In one embodiment, the treatment is treatment of a proliferative condition.

The terms "proliferative condition," "proliferative disorder," and "proliferative disease," are used interchangeably herein and pertain to an unwanted or uncontrolled cellular proliferation of excessive or abnormal cells that is undesired, such as, neoplastic or hyperplastic growth.

In one embodiment, the treatment is treatment of a proliferative condition characterised by benign, pre-malignant, or malignant cellular proliferation, including but not limited to, neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

In one embodiment, the treatment is treatment of cancer.

In one embodiment, the treatment is treatment of lung cancer, small cell lung cancer, gastrointestinal cancer, bowel cancer, colon cancer, rectal cancer, colorectal cancer, breast cancer, ovarian cancer, prostate cancer, testicular cancer, liver cancer, kidney cancer, bladder cancer, pancreas cancer, brain cancer, sarcoma, osteosarcoma, Kaposi's sarcoma, melanoma, malignant melanoma, basal cell carcinoma, or leukemia.

In one embodiment, the treatment is treatment of a condition mediated by HDAC.

The term "a condition mediated by HDAC," as used herein pertains to a condition in which HDAC and/or the action of HDAC is important or necessary, e.g., for the onset, progress, expression, etc. of that condition, or a condition that is known to be treated by HDAC inhibitors (such as, e.g., trichostatin A). One of ordinary skill in the art is readily able to determine whether or not a candidate HDACi treats a condition mediated by HDAC for any particular cell type. For example, assays which may conveniently be used to assess the activity offered by a particular compound are described in Watkins et al., 2002, international (PCT) patent publication number WO 02/30879.

Examples of such conditions include, but are not limited to, the following:

Cancer (see, e.g., Vigushin et al., 2001, *Clin. Cancer Res.*, Vol. 7, No. 4, pp. 971-976).

Psoriasis (see, e.g., Iavarone et al., 1999, *Mol. Cell Biol.*, Vol. 19, No. 1, pp. 916-922).

Fibroproliferative disorders (e.g., liver fibrosis) (see, e.g., Niki et al., 1999, *Hepatology*, Vol. 29, No. 3, pp. 858-867; Cornell et al., 1998, published Japanese patent application, publication number JP 10114681 A2).

Smooth muscle proliferative disorders (e.g., atherosclerosis, restenosis) (see, e.g., Kimura et al., 1994, *Biol. Pharm. Bull.*, Vol. 17, No. 3, pp. 399-402).

Neurodegenerative diseases (e g, Alzheimer's, Parkinson's, Huntington's chorea, amyotropic lateral sclerosis, spino-cerebellar degeneration) (see, e.g., Kuusisto et al., 2001, *Biochem. Biophys. Res. Commun.*, Vol. 280, No. 1, pp. 223-228; Stefan, J., et al., 2002, international (PCT) patent publication number WO 02/090534).

Inflammatory diseases (e.g., osteoarthritis, rheumatoid arthritis) (see, e.g., Dangond et al., 1998, *Biochem. Biophys. Res. Commun.*, Vol. 242, No. 3, pp. 648-652; Takahashi, I., et al, 1996, *J. Antibiot. (Tokyo)*, Vol. 49, No. 5, pp. 453-457).

Diseases involving angiogenesis (e.g., cancer, rheumatoid arthritis, psoriasis, diabetic retinopathy) (see, e.g., Kim et al., 2001, *Nature Medicine*, Vol. 7, No. 4, pp. 437-443).

Haematopoietic disorders (e.g., anaemia, sickle cell anaemia, thalassaeimia) (see, e.g., McCaffrey et al., 1997, *Blood*, Vol. 90, No. 5, pp. 2075-2083).

Fungal infections (see, e.g., Bernstein et al., 2000, *Proc. Natl. Acad. Sci. USA,* Vol. 97, No. 25, pp. 13708-13713; Tsuji et al., 1976, *J. Antibiot. (Tokyo)*, Vol. 29, No. 1, pp. 1-6).

Parasitic infections (e.g., malaria, trypanosomiasis, helminthiasis, protozoal infections (see, e.g., Andrews et al., 2000, *Int. J. Parasitol.*, Vol. 30, No. 6, pp. 761-768).

Bacterial infections (see, e.g., Onishi et al., 1996, *Science*, Vol. 274, pp. 939-940).

Viral infections (see, e.g., Chang et al., 2000, *Nucleic Acids Res.*, Vol. 28, No. 20, pp. 3918-3925).

Conditions treatable by immune modulation (e.g., multiple sclerosis, autoimmune diabetes, lupus, atopic dermatitis, allergies, asthma, allergic rhinitis, inflammatory bowel disease; and for improving grafting of transplants) (see, e.g., Dangond et al., 1998, *Biochem. Biophys. Res. Commun.*, Vol. 242, No. 3, pp. 648-652; Takahashi et al., 1996, *J. Antibiot. (Tokyo)*, Vol. 49, No. 5, pp. 453-457).

Dosing

Administration can be effected in one dose, continuously or intermittently (e.g., in divided doses at appropriate intervals) throughout the course of treatment. Methods of determining the most effective means and dosage of administration are well known to those of skill in the art and will vary with the particular formulation used for therapy, the purpose of the therapy, the target cell(s) being treated, and the subject being treated. Single or multiple administrations can be carried out with the dose level and pattern being selected by the treating physician, clinician, or veterinarian.

In one embodiment, the subject would receive the HDAC inhibitor intravenously or subcutaneously in quantities sufficient to deliver between about 3-1500 mg/m$^2$ per day, for example, about 3, 30, 60, 90, 180, 300, 600, 900, 1000, 1200, or 1500 mg/m$^2$ per day. Such quantities can be administered in a number of suitable ways, e.g., large volumes of low concentrations of HDAC inhibitor during one extended period of time or several times a day. The quantities can be administered for one or more consecutive days, alternate days, intermittent days, or a combination thereof per week (7 day period). Alternatively, low volumes of high concentrations of HDAC inhibitor during a short period of time, e.g., once a day for one or more days either consecutively, alternately, intermittently or a combination thereof per week (7 day period). For example, a dose of 300 mg/m$^2$ per day can be administered for 5 consecutive days for a total of 1500 mg/m$^2$ per treatment. In another dosing regimen, the number of consecutive days can also be 5, with treatment lasting for 2 or 3 consecutive weeks for a total of 3000 mg/m$^2$ and 4500 mg/m$^2$ total treatment.

Typically, an intravenous formulation can be prepared which contains a concentration of HDAC inhibitor of from about 1.0 mg/mL to about 10 mg/mL, e.g., 1.0 mg/mL, 2.0 mg/mL, 3.0 mg/mL, 4.0 mg/mL, 5.0 mg/mL, 6.0 mg/mL, 7.0 mg/mL, 8.0 mg/mL, 9.0 mg/mL and 10 mg/mL, and administered in amounts to achieve the doses described above. In one example, a sufficient volume of intravenous formulation can be administered to a subject in a day such that the total dose for the day is between about 300 and about 1200 mg/m$^2$.

In a specific embodiment, 900 mg/m$^2$ of PXD-101 is administered intravenously every 24 hours for at least five consecutive days. In another specific embodiment, 100 mg/m$^2$ of PXD-101 is administered intravenously every 24 hours for at least five consecutive days In another embodiment, oral dosages of HDAC inhibitors, when used to treat the desired condition, can range from about 2 mg to about 2000 mg per day, such as from about 20 mg to about 2000 mg per day, such as from about 200 mg to about 2000 mg per day. For example, oral dosages can be about 2, about 20, about 200, about 400, about 800, about 1200, about 1600 or about 2000 mg per day. It is understood that the total amount per day can be administered in a single dose or can be administered in multiple dosing such as twice, three, or four times per day.

For example, a subject can receive from about 2 mg/day to about 2000 mg/day, for example, from about 20 mg/day to about 2000 mg/day, such as from about 200 mg/day to about 2000 mg/day, for example from about 400 mg/day to about 1200 mg/day. A suitably prepared medicament for once a day administration can thus contain from about 2 mg to about 2000 mg, such as from about 20 mg to about 2000 mg, such as from about 200 mg to about 1200 mg, such as from about 400 mg/day to about 1200 mg/day. The HDAC inhibitors can be administered in a single dose or in divided doses of two, three, or four times daily. For administration twice a day, a suitably prepared medicament would therefore contain half of the needed daily dose.

Kits

One aspect of the present invention pertains to a kit (or kit-of-parts) comprising:
(a) a pharmaceutical composition (e.g., pre-formulation, formulation) as described herein, preferably provided in a suitable container and/or with suitable packaging; and
(b) instructions for use, for example, written instructions on how to administer the composition, etc.

One aspect of the present invention pertains to a kit (or kit-of-parts) comprising:
(a) a pharmaceutical composition (e.g., pre-formulation) as described herein, preferably provided in a suitable container and/or with suitable packaging; and
(b) instructions for use, for example, written instructions on how to prepare a suitable pharmaceutical formulation from the composition (e.g., pre-formulation), and how to subsequently administer the formulation, etc.

The kit may include additional parts, including, for example, appropriate solutions for dilution (e.g., physiological saline solution, glucose solution, etc.), reagents (e.g., for adjusting pH), and devices (e.g., bags, tubes, syringes, needles, transfer sets) for assembly and use (e.g., in the preparation of formulations and subsequent administration).

The written instructions may also include a list of indications for which the formulation (e.g., the HDACi therein) is a suitable treatment.

Formulation Studies

These studies demonstrate a substantial enhancement of HDACi solubility (on the order of a 500-fold increase for PXD-101) using one or more of: cyclodextrin, arginine, and meglumine. The resulting compositions are stable and can be diluted to the desired target concentration without the risk of precipitation. Furthermore, the compositions have a pH that, while higher than ideal, is acceptable for use.

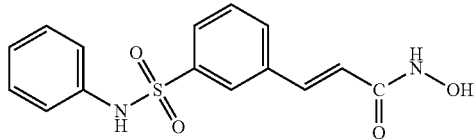

PXD-101

UV Absorbance

The ultraviolet (UV) absorbance $E^1_1$ value for PXD-101 was determined by plotting a calibration curve of PXD-101 concentration in 50:50 methanol/water at the $\lambda_{max}$ for the material, 269 nm. Using this method, the $E^1_1$ value was determined as 715.7. Methanol/water was selected as the subsequent diluting medium for solubility studies rather than neat methanol (or other organic solvent) to reduce the risk of precipitation of the cyclodextrin.

Solubility in Demineralised Water

The solubility of PXD-101 was determined to be 0.14 mg/mL for demineralised water.

Solubility Enhancement with Cyclodextrins

Saturated samples of PXD-101 were prepared in aqueous solutions of two natural cyclodextrins (α-CD and γ-CD) and hydroxypropyl derivatives of the α, β and γ cyclodextrins (HP-α-CD, HP-β-CD and HP-γ-CD). All experiments were completed with cyclodextrin concentrations of 250 mg/mL, except for α-CD, where the solubility of the cyclodextrin was not sufficient to achieve this concentration. The data are summarised in the following table. HP-β-CD offers the best solubility enhancement for PXD-101.

TABLE 1

Solubility Enhancement of Cyclodextrins

| Cyclodextrin | Cyclodextrin Concentration (mg/mL) | HDACi Concentration (mg/mL) | Solubility Enhancement |
|---|---|---|---|
| α-CD | 100 | 0.65 | 5 |
| HP-α-CD | 250 | 2.32 | 17 |
| HP-β-CD | 250 | 11.76 | 84 |
| γ-CD | 250 | 1.44 | 10 |
| HP-γ-CD | 250 | 7.00 | 50 |

Phase Solubility Determination of HP-β-CD

The phase solubility diagram for HP-β-CD was prepared for concentrations of cyclodextrin between 50 and 500 mg/mL (5-50% w/v). The calculated saturated solubilities of the complexed HDACi were plotted against the concentration of cyclodextrin. See FIG. 1.

The plot shows that there is an approximately linear relationship between cyclodextrin and HDACi concentration with a molar ratio of about 4:1. This type of phase solubility diagram for cyclodextrins is referred to as an A-Type phase solubility plot. The plot shows a slight positive deviation in the ratio of HDACi to cyclodextrin. This deviation may be due to experimental error caused by the decision to use of mass, instead of volume, to dispense the more concentrated cyclodextrin samples due to their viscosity. Alternatively, it is possible that there is a slight deviation from the linear A-Type phase solubility behaviour.

Concentrations of HP-β-CD between 250 and 300 mg/mL are typically used to produce isotonic solutions for injection formulations so a cyclodextrin concentration of 250 mg/mL or 25% w/v was selected for further studies.

pH Solubility Profile

The pH solubility profile for 25% w/v HP-β-CD was prepared using a variety of buffer systems as defined in *Buffers for pH and Metal Ion Control*, D. Perrin & B. Dempsey, Chapman & Hall, New York, 1983. Since cyclodextrin might complex with the buffering agents, appropriate selection of buffer systems was important: succinic acid/NaOH buffer was selected for pH 4; phosphate buffer was selected for the pH range 6-8; and glycine/NaOH buffer was selected for the pH range 8-9.

It was noted that zwitterions can be self-buffering and this effect caused some instability in the buffering capacity of the buffer systems at high pH. Therefore, the required pH could only be achieved by adjusting the pH of the system by the addition of 1 M NaOH.

Figure 2:
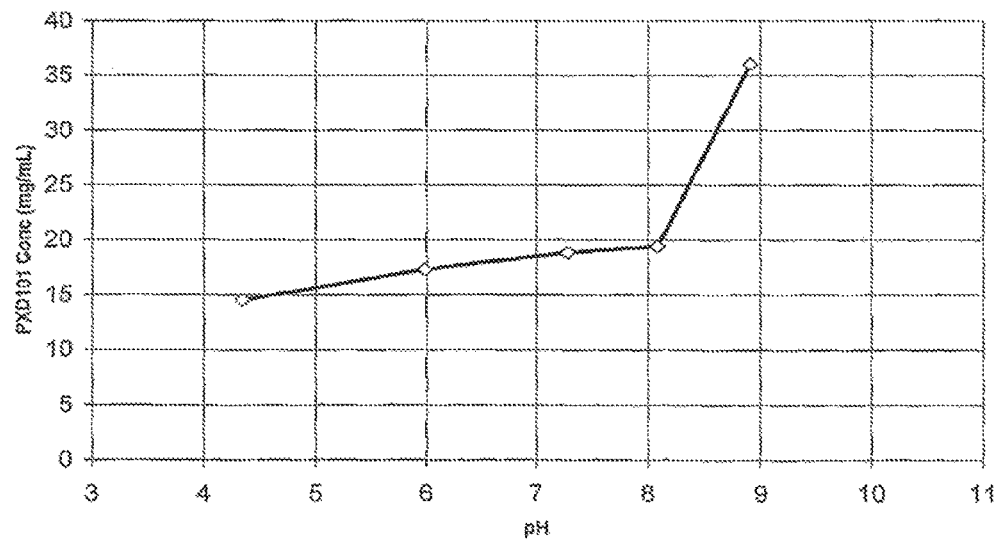
FIG. 2 is a buffered pH cyclodextrin solubility profile, and is a plot of HDACi (PXD-101) concentration (mg/mL) versus pH, for 25% w/v HP-β-CD.

The data are summarised in the following table. The pH solubility profile is shown in FIG. 2.

TABLE 2 pH Profile Data

| | | | | | |
|---|---|---|---|---|---|
| Target pH | 4 | 6 | 7.4 | 9.5 | * |
| Actual pH | 4.35 | 5.99 | 7.28 | 8.09 | 8.91 |
| PXD-101 Conc. (mg/mL) | 14.5 | 17.3 | 18.8 | 19.4 | 36.0 |

* pH adjusted with 1M NaOH to give actual pH

A yellow colouration was observed in all the samples prepared above pH 6, which was stronger as the pH increased. Observing that the concentration of the samples between pH 6 and 8 does not significantly change, it was concluded that the colour change was associated with pH. This conclusion was supported by a reduction in the intensity of colour in samples during pH adjustment.

Solubility Enhancement with In Situ Salts Formers

Initial experiments with acidic and basic in situ salt formers were based upon an assumption that a one-to-one salt would be formed between the salt former and the HDACi. On the basis of a preferred HDACi (PXD-101) concentration of 50 mg/mL (corresponding to 0.157 M), solutions of the salt former with a concentration of ~0.16 M were prepared.

Acidic In Situ Salts Formers

Acidic in situ salt formers proved to be ineffective in improving the solubility of PXD-101. The data are summarised in the following table. The decrease in calculated solubility for ascorbic acid suggests a chemical interaction or a salting out effect.

TABLE 3

Solubility Enhancement of Acidic in situ Salt Formers

| Salt Former | Salt Conc. (mg/mL)[1] | HDACi Solubility (mg/mL) | Solubility Enhancement | S/D[2] Molar ratio | pH of Solution |
|---|---|---|---|---|---|
| Lactic Acid | 14.2 | 0.16 | 1.1 | 316 | 2.38 |
| Ascorbic Acid | 27.7 | 0.01 | 0.1 | 4363 | 2.58 |
| Lactobionic Acid | 56.3 | 0.15 | 1.1 | 328 | 2.43 |
| Methanesulphonic Acid | 15.1 | 0.15 | 1.0 | 341 | 1.35 |
| Isethionate | 19.8 | 0.18 | 1.3 | 280 | 7.40 |
| Maleic Acid | 18.3 | 0.18 | 1.3 | 285 | 1.65 |
| Succinic Acid | 18.6 | 0.18 | 1.3 | 278 | 2.45 |
| Malic Acid | 21.1 | 0.16 | 1.2 | 309 | 2.19 |
| Glutamic Acid | 23.1 | 0.11 | 0.8 | 449 | 3.23 |

[1]Salt concentration equivalent to 0.16M.
[2]"S/D" molar ratio is "salt former-to-HDACi" ratio.

Basic In Situ Salts Formers

All of the basic in situ salt formers demonstrated a significant enhancement of the solubility of PXD-101 solubility. The data are summarised in the following table.

TABLE 4

Solubility Enhancement of Basic in situ Salt Formers

| Salt Former | Salt Conc. (mg/mL)[1] | HDACi Solubility (mg/mL) | Solubility Enhancement | S/D Molar ratio | pH of Solution |
|---|---|---|---|---|---|
| Arginine | 27.4 | 13.5 | 96 | 3.7 | 9.07 |
| Lysine | 23.0 | 12.0 | 86 | 4.2 | 9.11 |
| Meglumine | 30.7 | 21.2 | 152 | 2.4 | 9.22 |
| Triethanolamine | 23.5 | 2.8 | 20 | 17.8 | 8.80 |
| Diethanolamine | 16.5 | 10.5 | 75 | 4.8 | 9.13 |
| Tris | 19.0 | 3.6 | 26 | 13.7 | 8.97 |
| Ethylenediamine | 9.4 | 21.8 | 156 | 2.3 | 9.30 |

[1]Salt concentration equivalent to 0.16M

It was noted that the majority of the prepared samples were a strong yellow colour. Triethanolamine and tris were an exception, although this was probably due to the fact that the concentration of HDACi in solution was relatively low. The four basic salts that gave the highest solubility enhancement were: ethylenediamine, meglumine, L-arginine and L-lysine.

The saturated HDACi solutions were further tested in a series of dilution experiments (with 5% w/v glucose and 0.9% w/v saline solutions) to determine if the samples could be diluted to a desired infusion concentration of 3.5 mg/mL of HDACi. These experiments suggested an incompatibility between ethylenediamine and 5% w/v glucose solution. However the other salts could be diluted without evidence of precipitation.

Phase Solubility Diagrams for Arginine and Meglumine

Phase solubility diagrams for both arginine and meglumine were prepared using three further concentrations of these salt formers (×0.5, ×2, and ×3 the 0.16 M concentration used in the previous study), as set out in the following table.

TABLE 5

Concentrations of Basic in situ Salt Former

|  | x0.5 | x1 | x2 | x3 |
|---|---|---|---|---|
| Molarity | 0.079M | 0.157M | 0.314M | 0.47M |
| Arginine (mg/mL) | 13.7 | 27.4 | 54.8 | 82.2 |
| Meglumine (mg/mL) | 15.4 | 30.7 | 61.4 | 92.1 |

Figure 3:
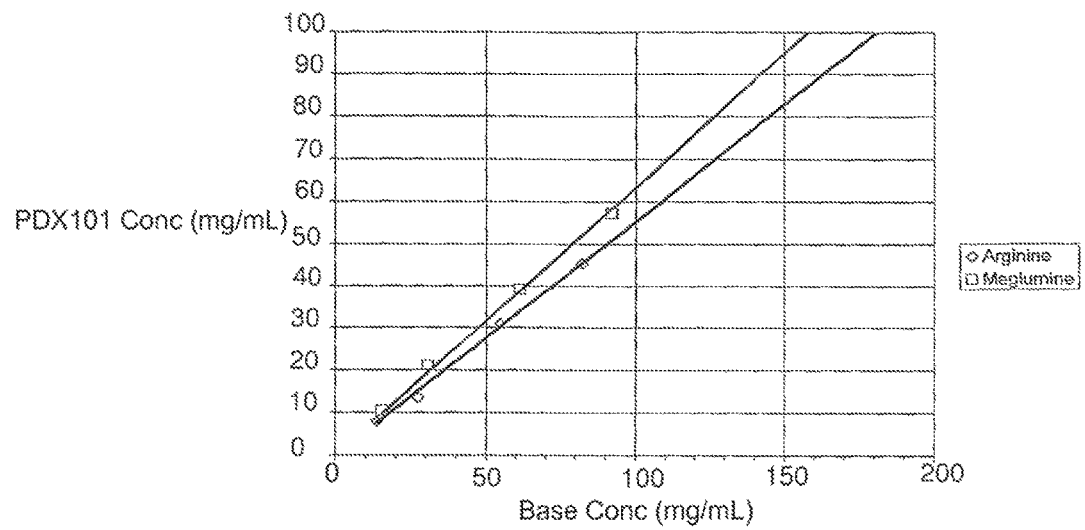
FIG. 3 is a phase solubility diagram for the in situ salt formers arginine and meglumine, and is a plot of HDACi (PXD-101) concentration (mg/mL) versus salt former (arginine (diamonds) or meglumine (squares)) concentration (mg/mL).

The data are summarised in the following table. The phase solubility diagrams are shown in FIG. 3. The plot shows that there is a linear relationship between solubility of HDACi and salt former concentration for both arginine and meglumine.

TABLE 6

Solubility Data

|  | 0.079 | 0.157 | 0.314 | 0.47 |
|---|---|---|---|---|
| Concentration of Arginine (M) | | | | |
| Arginine Concentration (mg/mL) | 13.7 | 27.4 | 54.8 | 82.2 |
| PXD-101 Concentration (mg/mL) | 7.9 | 13.5 | 31.1 | 45.3 |
| Concentration of Meglumine (M) | | | | |
| Meglumine Concentration (mg/mL) | 15.35 | 30.7 | 61.4 | 92.1 |
| PXD-101 Concentration (mg/mL) | 10.5 | 21.2 | 39.1 | 57.3 |

Using this linear relationship, it was possible to predict that both arginine and meglumine could be used to prepare HDACi concentrations of greater than 100 mg/mL. The minimum predicted concentrations of the basic in situ salt formers required for possible target HDACi (PXD-101) concentrations are summarised the following table.

TABLE 7

Predicted Salt Former Concentrations to Achieve Target HDACi Concentrations

| Target PXD-101 Conc. (mg/mL) | 50 mg/mL | 70 mg/mL | 100 mg/mL |
|---|---|---|---|
| Arginine Conc. (mg/mL) | 90.6 | 110.8 | 181.2 |
| Meglumine Conc. (mg/mL) | 79.2 | 126.9 | 158.3 |

Thus, it can be seen that approximately 1.8 parts of arginine is required to dissolve 1 part of HDACi (PXD-101), and approximately 1.6 parts of meglumine is required to dissolve 1 part of HDACi (PXD-101).

The pH of the saturated HDACi solutions increases slightly with increased concentration of salt former, with the arginine samples (pKa=9.0 (amine group)) having a slightly lower pH than the meglumine samples (pKa=9.5) at the same molar concentration. This difference is expected based on the pKa of the two salts. The data are summarised in the following table.

TABLE 8 pH of Basic Salt Former/PXD-101 Systems

|  | x0.5 | x1 | x2 | x3 |
|---|---|---|---|---|
| Molar Concentration of Basic Salt | 0.079M | 0.157M | 0.314M | 0.47M |
| Arginine (pH) | 9.10 | 9.07 | 9.19 | 9.22 |
| Meglumine (pH) | 9.22 | 9.20 | 9.33 | 9.40 |

Dilution Experiments

The 0.47 M arginine and 0.47 M meglumine saturated HDACi solutions were diluted with 5% w/v glucose and 0.9% w/v saline to give a target infusion concentration of 3.5 mg/mL of HDACi. These samples were successfully diluted and physically stable for more than 24 hours. The final pH of the diluted samples are summarised in the following table.

TABLE 9 pH of Diluted Salt Former/PXD-101 Systems

|  | HDACi Conc. of Sat'd Solution (mg/mL) | pH of Initial Saturated Solution | pH of Diluted Sample | |
|---|---|---|---|---|
|  |  |  | diluted with 5% w/v Glucose | diluted with 0.9% w/v Saline |
| 0.47M Arginine | 45.3 | 9.22 | 9.12 | 9.01 |
| 0.47M Meglumine | 57.3 | 9.40 | 9.20 | 9.17 |

Saturated samples were also diluted with pH 7.4 phosphate buffer, but with less success. Diluting 0.47 M and 0.314 M meglumine samples with pH 7.4 phosphate buffer instantly resulted in turbid solutions. Diluting 0.47 M and 0.314 M arginine samples with pH 7.4 phosphate buffer produced initially clear solutions but some crystallisation was noted after standing the diluted samples overnight at ambient temperature. This suggests that the diluted arginine samples are super-saturated and might be considered to be physically unstable. pH measurements of the buffer diluted samples showed that the pH had shifted to between pH 8.5 and 8.7, which was too low a pH to maintain PXD-101 in solution at the desired concentration of greater than or equal to 50 mg/mL.

Solubility Enhancement: Cyclodextrins & In Situ Salt Formers

Samples which contained 25% w/v HP-β-CD and 0.157 M or 0.314 M arginine or meglumine were prepared, and the solubility of HDACi (PXD-101) therein was studied. Surprisingly, the combination of cyclodextrin and salt former (arginine or meglumine) proved to be greatly synergistic, and provided a notable increase in HDACi solubility.

Figure 4:
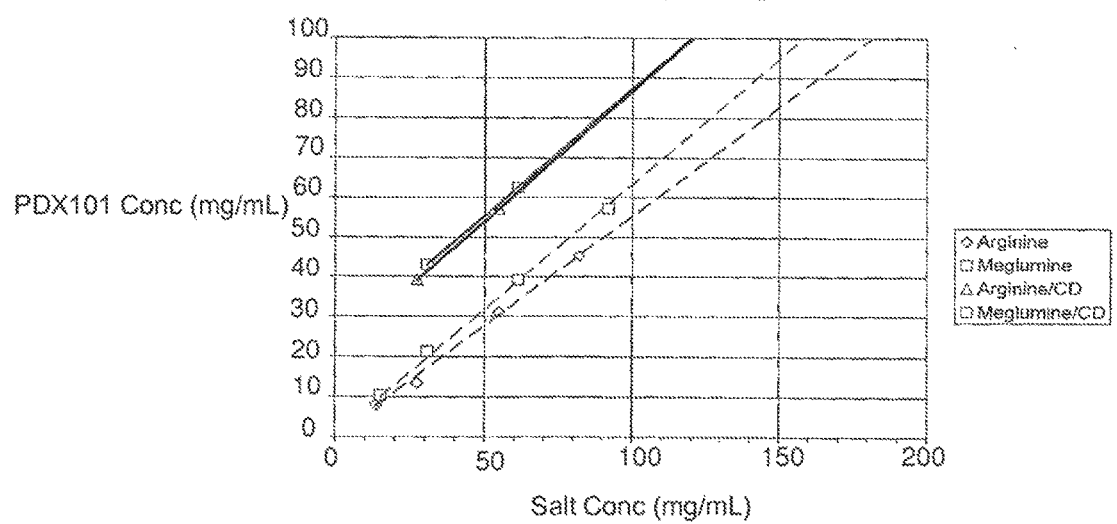
FIG. 4 is a phase solubility diagram for the combination of cyclodextrin and in situ salt formers arginine and meglumine, and is a plot of HDACi (PXD-101) concentration (mg/mL) versus salt former (arginine or meglumine) concentration (mg/mL), both with (solid lines; arginine=triangles; meglumine=squares) and without (dotted lines; arginine=diamonds; meglumine=squares) 25% w/v HP-β-CD.

The data are summarised in the following table. The phase solubility diagram is shown in FIG. 4.

TABLE 10

Solubility Data

|  | 0.157 | 0.314 |
|---|---|---|
| Molar Concentration of Arginine (M) | | |
| Arginine Concentration (mg/mL) | 27.4 | 54.8 |
| PXD-101 Concentration (mg/mL) | 39.2 | 57.1 |

TABLE 10-continued

Solubility Data

|  | 0.157 | 0.314 |
|---|---|---|
| Molar Concentration of Meglumine (M) | | |
| Meglumine Concentration (mg/mL) | 30.7 | 61.4 |
| PXD-101 Concentration (mg/mL) | 43.0 | 62.5 |

Figure 5:
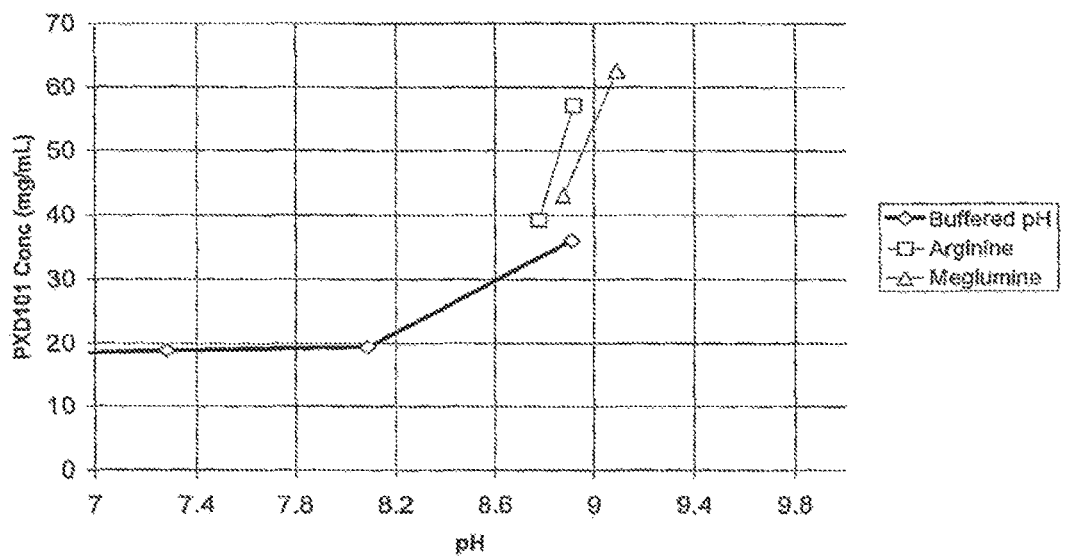
FIG. 5 is a pH profile diagram for the combination of cyclodextrin and in situ salt formers arginine and meglumine, and is a plot of HDACi (PXD-101) concentration (mg/mL) versus pH for phosphate buffer (diamonds), arginine (squares), or meglumine (triangles), each with 25% w/v HP-β-CD.

By also plotting the HDACi concentration against the pH of the salt former/cyclodextrin systems and of the buffered pH/cyclodextrin systems (described above), it is shown that the solubility enhancement observed for salt formers is more than that which would be provided by solely a pH effect. The data are summarised in the following table. The pH profile is shown in FIG. 5. This observation provides further evidence that arginine and meglumine are acting as in situ salt formers.

TABLE 11 pH and Solubility Data

|  | 0.157 | 0.314 |
|---|---|---|
| Concentration of Arginine (M) | | |
| pH of Saturated Solution | 8.78 | 8.92 |
| PXD-101 Concentration (mg/mL) | 39.2 | 57.0 |
| Concentration of Meglumine (M) | | |
| pH of Saturated Solution | 8.88 | 9.09 |
| PXD-101 Concentration (mg/mL) | 43.0 | 62.5 |

By employing the in situ salt former/cyclodextrin system, higher concentrations of HDACi could be achieved with the addition of less salt former. Consequently, this system produces a HDACi concentrate with a lower pH than a system where only salt former is use. The data are summarised in the following table.

TABLE 12 pH of Salt Former/Cyclodextrin/PXD-101 Systems

|  | Molar Concentration of Basic Salt | |
|---|---|---|
|  | x0.5 0.079M | x1 0.157M |
| Arginine/HP-β-CD (pH) | 8.78 | 8.92 |
| Meglumine/HP-β-CD (pH) | 8.88 | 9.09 |

Dilutions of the HDACi solutions to give a target infusion concentration of 3.5 mg/mL of HDACi were successful with both 0.9% w/v saline and 5% w/v glucose. In many cases, the lower pH of the initial system led to lower pH in the diluted solution, which leads to better tolerance of the infusion by the subject. The data are summarised in the following table.

TABLE 13 pH of Diluted Salt Former/Cyclodextrin/PXD-101 Systems

| | HDACi Conc. of Sat'd Solution (mg/mL) | pH of Initial Saturated Solution | pH of sample diluted with 5% w/v Glucose | pH of sample diluted with 0.9% w/v Saline |
|---|---|---|---|---|
| 0.157M Arginine | 39.0 | 8.78 | 8.49 | — |
| 0.157M Meglumine | 43.0 | 8.88 | 8.67 | — |
| 0.314M Arginine | 57.0 | 8.92 | 8.90 | 8.96 |
| 0.314M Meglumine | 62.5 | 9.09 | 9.06 | 9.28 |

Further pH Adjustment

The pH of the systems containing arginine or meglumine is approximately 9. However, it is possible that the HDACi (e.g., PXD-101) is chemically unstable at a pH above 8.5. Therefore, attempts were made to lower the pH of the saturated systems using 2 N HCl, in an effort to improve the chemical stability of the HDACi.

To a 1 mL aliquot of the saturated sample was added 20 µL of 2 N HCl. The resulting sample was allowed to stabilise overnight and the new pH of the system recorded. Subsequently, 20 µL aliquots of 2 N HCl were rapidly added to the samples until precipitation was noted, the pH at each addition step being recorded. The data are summarised in the following table.

TABLE 14 pH Adjustment of Solubility Enhancement Systems

| | 0.47M Meglumine | 0.314M Arginine/ 25% HP-β-CD | 0.314M Meglumine/ 25% HP-β-CD |
|---|---|---|---|
| Initial pH | 9.40 | 8.92 | 9.09 |
| +20 µL HCl | 9.11 (solid formed at interface) | 8.85 (stable overnight) | 8.99 (stable overnight) |
| +40 µL HCl | — | 8.66 | 8.76 (possible turbid) |
| +60 µL HCl | — | 8.42 | 8.56 (turbid) |
| +80 µL HCl | — | 8.22 (turbid) | — |

A reduction of the strong yellow tint of the samples was noted with the addition of the HCl. This observation is consistent with the earlier conclusion that the colouration of PXD-101 is pH dependent and is not a direct indication of decomposition.

The results indicate that the basic salt former/cyclodextrin system is more stable than the system containing only the basic salt former. The observations from the 0.47 M meglumine sample suggested that the solid only formed at the interface between the introduced volume of HCl and the saturated HDACi solution—this solid would not dissolve upon shaking and no further precipitation/turbidity occurred. More successful pH adjustment may be possible with a weaker or more dilute acid.

The results also suggest that the arginine/cyclodextrin system is more physically stable than the meglumine/cyclodextrin system; however, it should be noted that the initial concentration of the meglumine system is 5 mg/mL higher.

EXAMPLES

The following are examples are provided solely to illustrate the present invention and are not intended to limit the scope of the invention, as described herein.

Example 1

Preparation of PXD-101 Solution in L-Arginine

A 10 g quantity of L-arginine was added to a vessel containing approximately 70 mL of Water-For-Injections BP. The mixture was stirred with a magnetic stirrer until the arginine had dissolved. A 5 g quantity of PXD-101 was added, and the mixture stirred at 25° C. until the PXD-101 had dissolved. The solution was diluted to a final volume of 100 mL using Water-For-Injections BP. The resulting solution had a pH of 9.2-9.4 and an osmolality of approximately 430 mOSmol/kg.

Sterilisation and Filling

The solution was filtered through a suitable 0.2 µm sterilising (e.g. PVDF) membrane. The filtered solution was placed in vials or ampoules, which were sealed by heat, or with a suitable stopper and cap.

Storage of Solutions

The solutions were stored at ambient temperature, or, more preferably, under refrigeration (e.g., 2-8° C.) in order to reduced degradation of the HDACi.

Example 2

Intravenous Dosing of PXD-101

Background

PXD 101 is a low molecular weight histone deacetylase (HDAC) inhibitor with a sulfonamide-hydroxamide structure. HDAC inhibitors modulate transcriptional activity of genes important for tumor growth and survival. PXD 101 has potent antiproliferative activity against cell lines from multiple cancer types in vitro, and demonstrates antineoplastic activity in animal tumor models. PXD 101 reduces tumor volume of human xenografts. In addition, PXD 101 has synergistic and additive anti-tumor activity in vitro and in vivo, in combination with many established anticancer therapeutics.

Objectives

To determine the safety, dose-limiting toxicity (DLT), and maximum tolerated dose (MTD) of PXD 101 (in solution with L-arginine) administered as a 30-min I.V. infusion on days 1 to 5 every 3 weeks, in subjects with advanced cancer; to determine plasma pharmacokinetic parameters for PXD 101 following I.V. administration at varying dose levels; and to investigate the pharmacodynamic effects of PXD 101 in blood mononuclear cells following I.V. administration at varying dose levels.

Subjects

Subjects with advanced cancer refractory to standard therapy or for whom no standard therapy exists, age≥18 years, ECOG score≤2. The relevant characteristics for the subjects in this study are summarized in the following table.

TABLE 15

Characteristics of Subjects

| Number of Subjects | — | 28 |
|---|---|---|
| Gender | Male | 14 |
| | Female | 14 |

TABLE 15-continued

Characteristics of Subjects

| Age | Median | 59 years |
|---|---|---|
|  | Range | 28-74 years |
| Race | White | 28 |
|  | Non-White | 0 |
| ECOG PS | Score 0 | 7 |
|  | Score 1 | 20 |
|  | Score 2 | 1 |
| Cancer Diagnosis | Colorectal | 9 |
|  | Melanoma | 5 |
|  | Oesophageal | 2 |
|  | Ovarian | 1 |
|  | Renal | 1 |
|  | Prostate | 2 |
|  | Breast | 1 |
|  | Cervical | 1 |
|  | Other | 6 |

Dosing Schedule

PXD-101 was administered as a 30-minute intravenous infusion on days 1 to 5 every 3 weeks to subjects with advanced cancer. Sequential dose cohorts of 3-6 subjects were examined (150, 300, 600, 900, and 1200 mg/m$^2$), followed by examination of an expanded cohort at 1000 mg/m$^2$ for I.V. and oral testing. The treatment doses and cycles are summarized in the following table.

TABLE 16

Treatment Doses and Cycles

| Dose (mg/m$^2$) | Number of Subjects | Total Number of Cycles | Range of Cycles at Each Dose |
|---|---|---|---|
| 150 | 4 | 9 | 1-4 |
| 300 | 4 | 9 | 1-4 |
| 600 | 6 | 16 | 1-6 |
| 900 | 3 | 13 | 1-9 |
| 1200 | 6 | 15 | 1-9 |
| 1000 | 6 | 10 | 1-3 |

Results

Plasma PK analysis was performed for subjects of all dose groups on days 1 and 5 of cycle 1 following 30 minutes of I.V. infusion. The PK analysis is summarized in the following table.

TABLE 17

Summary of PK Analysis

| Dose (mg/m$^2$) | Cmax (ng/mL) | $t_{1/2}$ (min) | $V_d$ (L/m$^2$) | $CL_s$ (L/hr/m$^2$) | AUC$_{0-t}$ (ngxhr/mL) | AUC$_{0-t}$/ AUC$_{0-\infty}$ (%) | AUC$_{day\,5}$/ AUC$_{day\,1}$ (%) |
|---|---|---|---|---|---|---|---|
| 150 | 6565 ± 2158 | 46.6 ± 8.7 | 115.1 ± 43.5 | 122.6 ± 30.6 | 1269 ± 272 | 99.0 ± 0.7 | 115 ± 22 |
| 300 | 15505 ± 6245 | 44.6 ± 8.0 | 88.8 ± 31.8 | 94.6 ± 34.9 | 3497 ± 1097 | 99.7 ± 0.1 | 112 ± 21 |
| 600 | 31177 ± 8968 | 43.4 ± 6.7 | 57.6 ± 13.9 | 59.6 ± 16.0 | 10707 ± 3008 | 99.9 ± 0.0 | 97 |
| 900 | 53779 ± 6381 | 54.2 ± 8.7 | 48.8 ± 9.8 | 63.5 ± 16.4 | 14746 ± 3407 | 99.8 ± 0.1 | NA |
| 1200 | 52362 ± 12724 | 85.5 ± 19.6 | 90.2 ± 87.3 | 66.6 ± 33.5 | 22012 ± 10979 | 99.8 ± 0.1 | NA |

Figure 6:
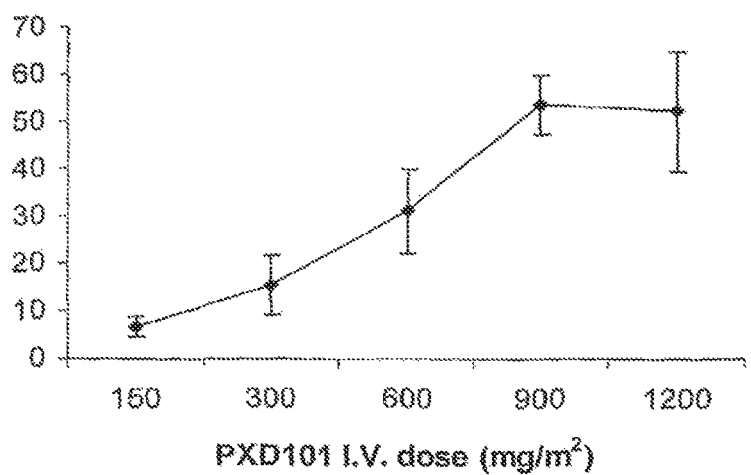
FIG. 6 is a graph showing the mean Cmax (±SD) of I.V. PXD101 on day 1, measured in 2-4 subjects at each dose level.
Figure 7:
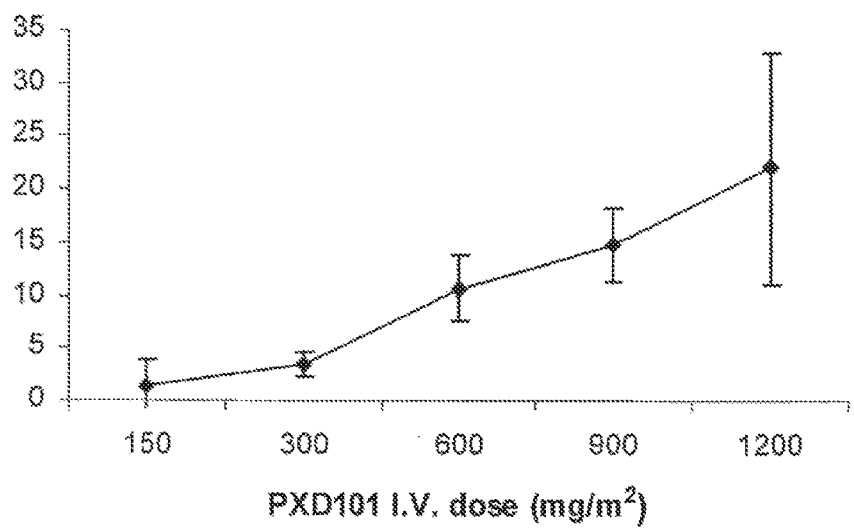
FIG. 7 is a graph showing the mean AUC (±SD) of I.V. PXD101 on day 1, measured in 2-4 subjects at each dose level.
Figure 8:
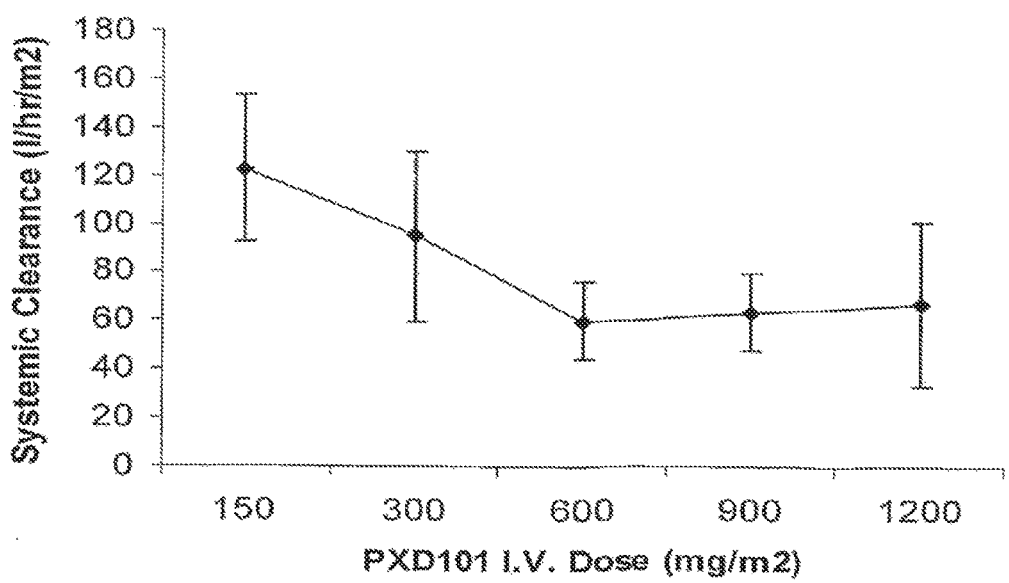
FIG. 8 is a graph showing the mean clearance (±SD) of I.V. PXD101 on day 1, measured in 2-4 subjects at each dose level.

Pharmacokinetic analysis shows dose proportional plasma levels and AUC, with an elimination half-life of 47-86 minutes. (See FIG. 6, FIG. 7, FIG. 8). There was no HDACi accumulation on repeated dosing.

PXD-101 was generally well-tolerated at doses up to 1000 mg/m$^2$. The main HDACi-related adverse events were fatigue, nausea, vomiting (infusion-related), and phlebitis. Nausea and vomiting frequently required anti-emetic therapy. Other adverse events included headache, diarrhoea, constipation, and dyspnoea. No specific abnormalities were detected in laboratory tests. In particular, no hematological toxicity was identified. At least one subject experienced Grade 3 fatigue at 600 mg/m$^2$. Atrial fibrillation, which was spontaneously reversible, occurred at 1200 mg/m$^2$. Grade 3 diarrhoea and lethargy prevented completion of a cycle at 1200 mg/m$^2$.

Pharmacodynamic Analysis

Figure 9:
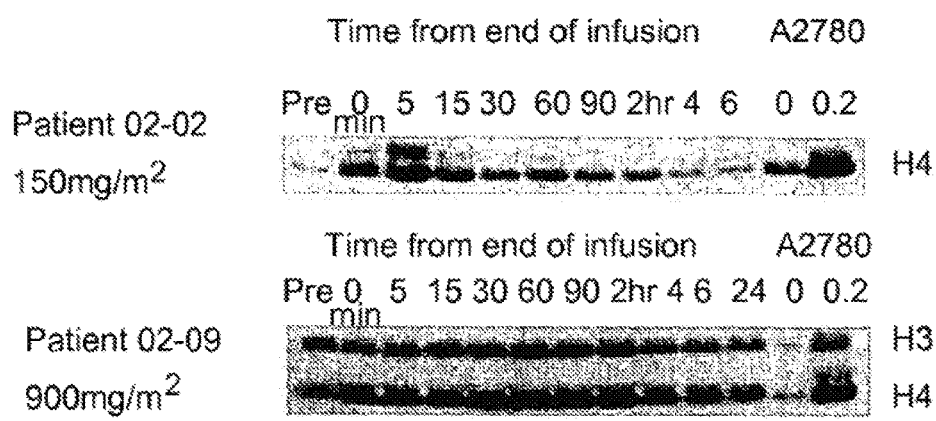
FIG. 9 is a Western blot showing histone H3 and H4 acetylation in peripheral blood mononuclear cells at the indicated times post-dose.
Figure 10:
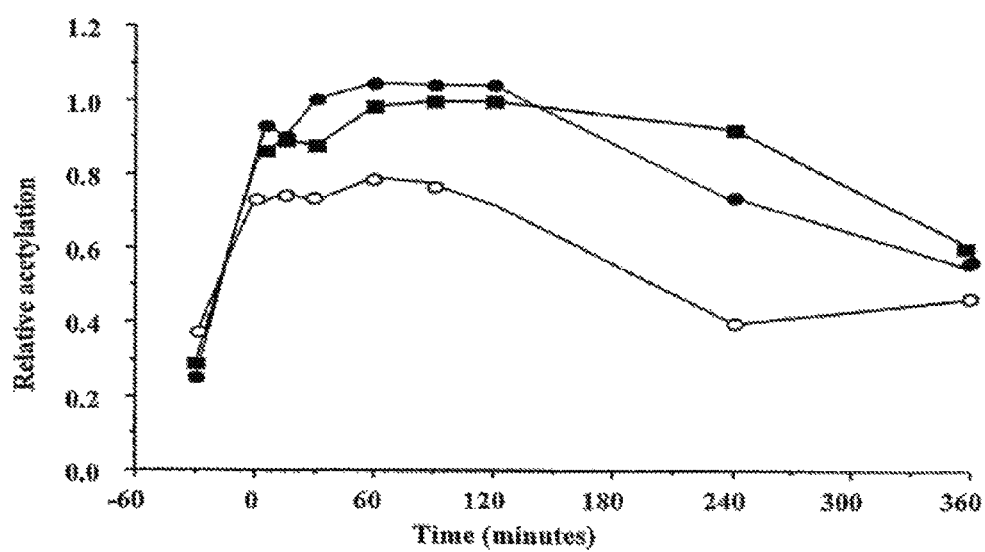
FIG. 10 is a graph showing acetylation expressed as a densitometric measurement of H4 acetylation in PBMC samples relative to H4 in a treated cell line standard (A2780) as a function of time.

Peripheral blood mononuclear cells were collected pre-therapy, immediately post-infusion, and between 2-24 hours after intravenous administration of PXD-101 to assess the effect of PXD-101 on the extent of histone acetylation in a normal host cell. Histones were isolated and probed with anti-acetylated histone (H4 and/or H3) antibody followed by HRP-secondary antibody. Preliminary analysis demonstrated an increase in the accumulation of acetylated histones in peripheral mononuclear cells that could be detected up to 24 hours after intravenous administration of PXD-101. See FIG. 9 and FIG. 10. Dose proportional H4 acetylation was observed, with a more sustained effect at higher doses.

Figure 11:
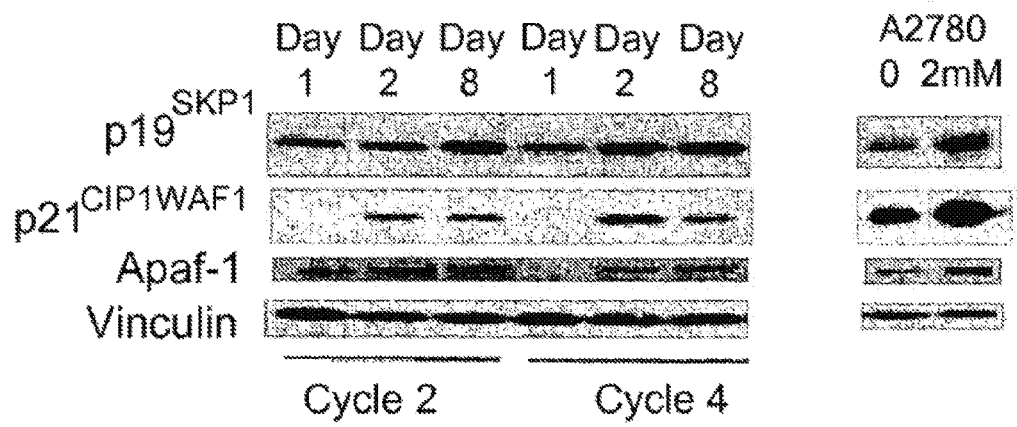
FIG. 11 is a Western blot showing the expression of proteins (p19$^{SKP1}$, p21$^{CIP1WAF1}$, Apaf-1 and vinculin) involved in cell-cycle arrest and apoptosis from lymphocytes prepared from a subject during cycles 2 and 4 of PXD101 treatment at 900 mg/m².

The expression of proteins involved in cell cycle arrest and apoptosis (e.g., p19$^{SKP1}$, p21$^{CIP1\,WAF1}$, Apaf-1 and vinculin) were measured on days 1, 2 and 8 of each cycle. FIG. 11 is a Western Blot showing expression of these proteins taken from lymphocytes prepared from a subject during cycles 2 and 4 of PXD-101 treatment at 900 mg/m$^2$.

Example 3

Oral Administration of PXD-101

Figure 12:
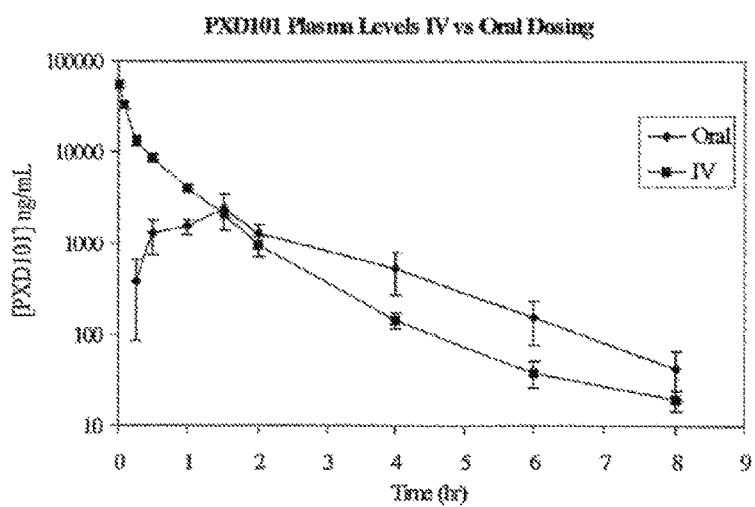
FIG. 12 is a graph showing I.V. and oral data from the same 3 subjects (oral dose given on day 1, cycle 3) at 900 and 1200 mg/m². Plasma levels normalized for 900 mg/m² dosing assuming dose proportionality. Values=mean±SE.

Several subjects received PXD-101 in an oral formulation (e.g., PXD-101 in a gelatin capsule). Preliminary data with oral dosing showed good tolerability. Bioavailability for the oral formulation was approximately 33%. FIG. 12 is a graph comparing plasma levels following oral and intravenous administration of PXD-101. The plasma levels remain higher when dosed orally.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention as defined herein.

What is claimed:
1. A pharmaceutical composition comprising:
(a) a histone deacetylase (HDAC) inhibitor;
(b) cyclodextrin; and
(c) meglumine:
wherein said HDAC inhibitor is selected from compounds of the following formula and pharmaceutically acceptable salts thereof:

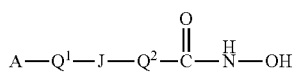

wherein:
A is a substituted or unsubstituted:
$C_{6-20}$carboaryl, or
$C_{5-20}$heteroaryl;
$Q^1$ is:
a covalent bond, or
a substituted or unsubstituted
$C_{1-7}$alkylene,
$C_{2-7}$alkenylene;
J is:
—$NR^N$—$S(=O)_2$—, or
—$S(=O)_2$—$NR^N$—;
$R^N$ is:
—H, or
a substituted or unsubstituted
$C_{1-7}$alkyl,
$C_{3-20}$heterocyclyl,
$C_{6-20}$carboaryl,
$C_{5-20}$heteroaryl,
$C_{6-20}$carboaryl-$C_{1-7}$alkyl, or
$C_{5-20}$heteroaryl-$C_{1-7}$alkyl;
$Q^2$ is a substituted or unsubstituted:
$C_{6-20}$carboarylene,
$C_{5-20}$heteroarylene,
$C_{6-20}$carboarylene-$C_{1-7}$alkylene,
$C_{5-20}$heteroarylene-$C_{2-7}$alkylene,
$C_{6-20}$carboarylene-$C_{2-7}$alkenylene,
$C_{5-20}$heteroarylene-$C_{2-7}$alkenylene,
$C_{1-7}$alkylene-$C_{6-20}$carboarylene,
$C_{1-7}$alkylene-$C_{5-20}$heteroarylene,
$C_{2-7}$alkenylene-$C_{6-20}$carboarylene,
$C_{2-7}$alkenylene-$C_{5-20}$heteroarylene,
$C_{1-7}$alkylene-$C_{6-20}$carboarylene-$C_{1-7}$alkylene,
$C_{1-7}$alkylene-$C_{5-20}$heteroarylene-$C_{1-7}$alkylene,
$C_{2-7}$alkenylene-$C_{6-20}$carboarylene-$C_{1-7}$alkylene,
$C_{2-7}$alkenylene-$C_{5-20}$heteroarylene-$C_{1-7}$alkylene,
$C_{1-7}$alkylene-$C_{6-20}$carboarylene-$C_{2-7}$alkenylene,
$C_{1-7}$alkylene-$C_{5-20}$heteroarylene-$C_{2-7}$alkenylene,
$C_2$-7alkenylene-$C_{6-20}$carboarylene-$C_{2-7}$alkenylene, or
$C_{1-7}$alkenylene-$C_{5-20}$heteroarylene-$C_{2-7}$alkenylene,
and is unsubstituted or substituted.
2. A pharmaceutical composition according to claim 1, wherein the HDAC inhibitor is selected from the following compounds and pharmaceutically acceptable salts thereof:

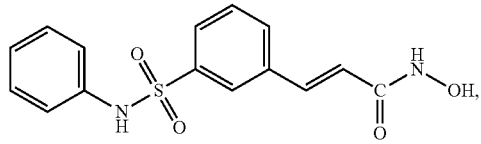

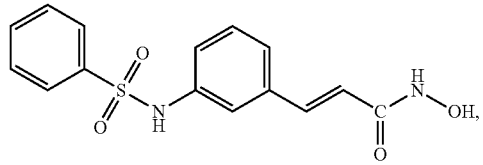

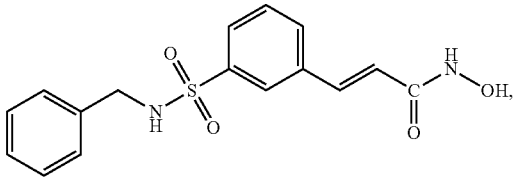

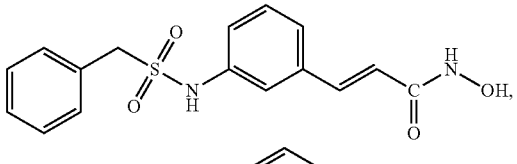

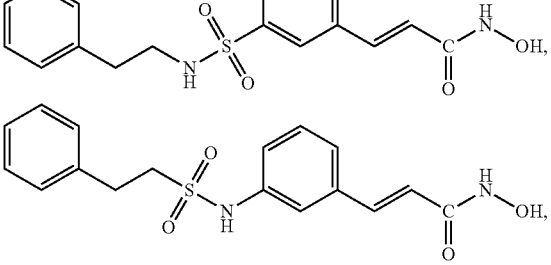

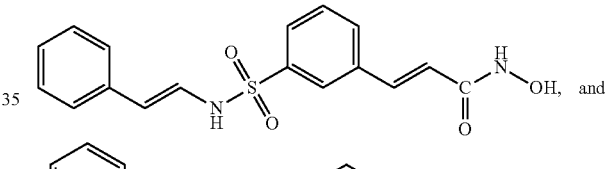

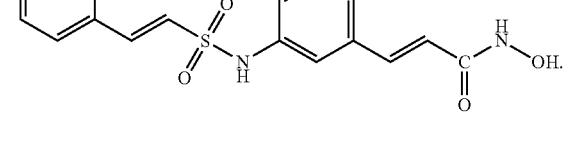

3. A pharmaceutical composition according to claim 1, wherein the HDAC inhibitor is selected from the following compound and pharmaceutically acceptable salts thereof:

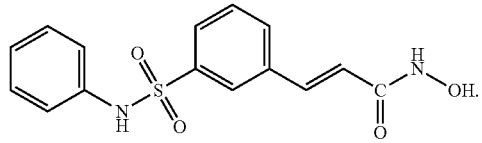 [SMILES: O=C(/C=C/c1cccc(S(=O)(=O)Nc2ccccc2)c1)NO]

4. A pharmaceutical composition according to claim 1, wherein said cyclodextrin is selected from:
α-cyclodextrin; β-cyclodextrin; γ-cyclodextrin;
(C1-4alkyl)-α-cyclodextrin; (C1-4alkyl)-β-cyclodextrin; (C1-4alkyl)-γ-cyclodextrin;
(hydroxy-C1-4alkyl)-α-cyclodextrin; (hydroxy-C1-4alkyl)-β-cyclodextrin; (hydroxy C1 4alkyl)-γ-cyclodextrin;
(carboxy-C1-4alkyl)-α-cyclodextrin; (carboxy-C1-4alkyl)-β-cyclodextrin; (carboxy C1 4alkyl)-γ-cyclodextrin;

saccharide ethers of α-cyclodextrin; saccharide ethers of β-cyclodextrin; saccharide ethers of γ-cyclodextrin; sulfobutyl ethers of α-cyclodextrin, β-cyclodextrin, and γ-cyclodextrin.

5. A pharmaceutical composition according to claim 1, wherein said cyclodextrin is hydroxypropyl-β-cyclodextrin.

6. A pharmaceutical composition according to claim 1, wherein the molar ratio of cyclodextrin to said HDAC inhibitor is from 0.5 to 5.

7. A pharmaceutical composition according to claim 1, which is a liquid.

8. A pharmaceutical composition according to claim 1, which comprises said HDAC inhibitor at a concentration of 0.1-1000 mg/mL.

9. A pharmaceutical composition according to claim 1, which comprises said HDAC inhibitor at a concentration of 30-300 mg/mL.

10. A pharmaceutical composition according to claim 1, which comprises said HDAC inhibitor at a concentration of 0.3-3000 mM.

11. A pharmaceutical composition according to claim 1, which comprises said HDAC inhibitor at a concentration of 100-500 mM.

12. A pharmaceutical composition according to claim 1, which comprises said HDAC inhibitor at a concentration of 0.01-300 mg/mL.

13. A pharmaceutical composition according to claim 1, which comprises said HDAC inhibitor at a concentration of 1.0-10 mg/mL.

14. A pharmaceutical composition according to claim 1, which comprises said HDAC inhibitor at a concentration of 0.01-100 mM.

15. A pharmaceutical composition according to claim 1, which comprises said HDAC inhibitor at a concentration of 3-30 mM.

16. A pharmaceutical composition according to claim 1, wherein said composition is suitable for parenteral administration to a patient.

17. A pharmaceutical composition according to claim 7, wherein said composition is suitable for administration to a patient by injection or infusion.

18. A pharmaceutical composition according to claim 1, which is a solid.

19. A pharmaceutical composition according to claim 1, which is in the form of a powder, granules, tablets, or a lyophilate/lyophilisate.

20. An intravenous (IV) infusion bag, a vial or an ampoule containing a pharmaceutical composition according to claim 7.

* * * * *